(12) United States Patent
Shapiro et al.

(10) Patent No.: US 7,189,856 B2
(45) Date of Patent: Mar. 13, 2007

(54) NON-PEPTIDE SOMATOSTATIN RECEPTOR LIGANDS

(76) Inventors: Gideon Shapiro, 5507 NW. 80th Ave., Gainesville, FL (US) 32653; Michael G. Natchus, 555 Waterview Trail, Alpharetta, GA (US) 30022; Mark A. Lockwood, 5315 John's View St., Alpharetta, GA (US) 30005; Simona Jurczyk, 4830 NW. 43rd St., Gainesville, FL (US) 32606

( * ) Notice: Subject to any disclaimer, the term of this patent is extended or adjusted under 35 U.S.C. 154(b) by 258 days.

(21) Appl. No.: 10/289,924

(22) Filed: Nov. 7, 2002

(65) Prior Publication Data
US 2003/0191134 A1 Oct. 9, 2003

Related U.S. Application Data

(60) Provisional application No. 60/344,564, filed on Dec. 28, 2001, provisional application No. 60/344,563, filed on Dec. 28, 2001.

(51) Int. Cl.
C07D 27/104 (2006.01)
A61K 31/41 (2006.01)

(52) U.S. Cl. ............... 548/125; 514/359; 514/396

(58) Field of Classification Search ......... 548/125; 514/359, 396
See application file for complete search history.

(56) References Cited

U.S. PATENT DOCUMENTS

| | | | |
|---|---|---|---|
| 5,776,894 A | 7/1998 | Albert et al. | |
| 6,025,372 A | 2/2000 | Yang et al. | |
| 6,057,338 A | 5/2000 | Yang et al. | |
| 6,063,796 A | 5/2000 | Yang et al. | |
| 6,117,880 A | 9/2000 | Guo et al. | |
| 6,225,284 B1 | 5/2001 | Albert et al. | |
| 6,241,965 B1 | 6/2001 | Dean et al. | |
| 6,262,229 B1 | 7/2001 | Coy et al. | |

(Continued)

FOREIGN PATENT DOCUMENTS

EP 0 615 630 A2 12/1985

(Continued)

OTHER PUBLICATIONS

Fetter et al, Hydantoins, thiohydantoins, glycocyamidnes . . . Acta Chimica Academiae Scientaiarum Hungaricae (1973), 78(3), 325-33.*

(Continued)

*Primary Examiner*—James O. Wilson
*Assistant Examiner*—Paul V. Ward
(74) *Attorney, Agent, or Firm*—Saliwanchik, Lloyd & Saliwanchik

(57) ABSTRACT

Non-peptide somatostatin receptor ligands with conformationally restricted side chains exhibiting high binding affinity toward somatostatin receptors are provided. The compounds exhibit a high selectivity and act as agonists at human subtype 2 somatostatin receptors. The compounds are long acting for advantageous use as medicaments in peripheral diseases where somatostatinergic therapy is indicated. Furthermore, many of the compounds are lipophilic and are particularly useful for treating central nervous system and ophthalmic diseases where penetration of the blood brain and blood retinal barriers is required. It is a further object to describe the preferred stereoisomers of these somatostatin agonists and processes for their preparation. Further objects will become apparent from reading the following description.

18 Claims, 2 Drawing Sheets

Example 15a Human SSTR2 Binding

U.S. PATENT DOCUMENTS

| | | | |
|---|---|---|---|
| 6,265,375 | B1 | 7/2001 | Gilon et al. |
| 6,268,342 | B1 | 7/2001 | Culler et al. |
| 6,294,520 | B1 | 9/2001 | Naito |
| 6,316,004 | B1 | 11/2001 | Lunin et al. |
| 6,316,414 | B1 | 11/2001 | Burman et al. |
| 6,344,358 | B1 | 2/2002 | Matsuoka et al. |
| 6,346,601 | B1 | 2/2002 | Obiols et al. |
| 6,352,982 | B1 | 3/2002 | Mabuchi et al. |
| 6,355,613 | B1 | 3/2002 | Hornik et al. |
| 6,358,491 | B1 | 3/2002 | Lister-James et al. |
| 6,387,932 | B1 | 5/2002 | Zhou et al. |
| 2001/0011072 | A1 | 8/2001 | Culler et al. |
| 2001/0025097 | A1 | 9/2001 | Sheridan et al. |
| 2002/0016298 | A1 | 2/2002 | Hay et al. |
| 2002/0052315 | A1 | 5/2002 | Hornik et al. |

FOREIGN PATENT DOCUMENTS

| | | |
|---|---|---|
| GB | 642159 | 8/1950 |
| GB | 643089 | 9/1950 |
| GB | 652207 | 4/1951 |
| GB | 985966 | 3/1965 |
| GB | 2 227 488 | 8/1990 |
| GB | 2 351 733 | 1/2001 |
| WO | WO 98/44921 A1 | 10/1998 |
| WO | WO 98/44922 A1 | 10/1998 |
| WO | WO 98/45285 A1 | 10/1998 |
| WO | WO 99/22735 A1 | 5/1999 |
| WO | WO 00/61587 A1 | 10/2000 |
| WO | WO 00/70347 A1 | 11/2000 |
| WO | WO 00/75186 A1 | 12/2000 |
| WO | WO 01/00676 A1 | 1/2001 |
| WO | WO 01/07424 A1 | 2/2001 |
| WO | WO 01/09090 A2 | 2/2001 |
| WO | WO 01/85718 * | 11/2001 |
| WO | WO 01/85718 A1 | 11/2001 |
| WO | WO 02/09739 A1 | 2/2002 |
| WO | WO 02/10140 A2 | 2/2002 |
| WO | WO 02/10192 A2 | 2/2002 |
| WO | WO 02/10215 A1 | 2/2002 |
| WO | WO 02/26766 A2 | 4/2002 |

OTHER PUBLICATIONS

Albert, R., et al., "Direct Synthesis of [DOTA-Dphe$^1$]-Octreotide and [DOTA-Dphe$^1$,Tyr$^3$]-Octreotide (SMT487): Two Conjugates for Systemic Delivery of Radiotherapeutical Nuclides to Somatostatin Receptor Positive Tumors in Man", *Bioorg. Med. Chem. Lett.* (1998), 8:1207-1210; Elsevier Science Ltd.

Arnold, R., et al., "Somatostatin Analog Sandostatin and Inhibition of Tumor Growth in Patients with Metastatic Endocrine Gastroenteropancreatic Tumors", *World J. Surg.* (1993), 17:511-519; Société Internationale de Chirurgie.

Bauer, W., et al., "A very potent and selective octapeptide analog of somatostatin with prolonged action", *Life Sciences* (1982), 31:1133-40.

Guisti, et al., "Clinical results of long-term slow-release lanreotide treatment of acromegaly", *Euro. J. Clin. Investigation* (1997), 27(4):277-84.

Kessler, et al., "Peptide Conformations. 28. Relayed Heteronuclear Correlation Spectroscopy and Conformational Analysis of Cyclic Hexapeptides Containing the Active Sequence of Somatostatin," *J. Am. Chem. Soc.* (1983), 105:6944-6952.

Krenning, E.P., et al., "Somatostatin receptor scintigraphy with [$^{111}$In-DTPA-D-Phe$^1$]- and [$^{123}$I-Tyr$^3$]-octreotide: the Rotterdam Experience with more than 1000 patients", *Eur. J. Nuc. Med.* (1993), 20(8):715-731; Springer-Verlag.

Liebow, et al., "Somatostatin analogues inhibit growth of pancreatic cancer by stimulating tyrosine phosphatase", *Proc. Natl. Acad. Sci.* (1989), 86:2003-2007.

Pasternak, A., et al., "Potent, orally, bioavailable Somatostatin agonists: good absorption achieved by urea backbone cyclization", *Bioorg. Med. Chem. Lett.* (1999), 9(3):491-496.

Rohrer, et al., "Rapid Identification of Subtype-Selective Agonists of the Somatostatin Receptor Through Combinational Chemistry", *Science* (1998), 282:737-740.

Scicinski, J.J., et al., "The solid phase synthesis of a series of tri-substituted hydantoin ligands for the somatostatin SST5 receptor", *Bioorg. Med. Chem. Lett.* (1998), 8(24):3609-14.

Yang, et al., "Potent and Selective Non-Peptide Human Somatostatin Receptor Subtype-2 (hSSTR-2) agonists", Book of Abstracts, 216th ACS National Meeting, Boston, MA, Aug. 23-27 (1998); MEDJ-194.

Yang, et al., "Spiro[1H-indene-1,4-piperidine] Derivatives As Potent and Selective Non-Peptide Human Somatostatin Receptor Subtype 2 (sst$_2$) Agonists", *J. Med. Chem.* (1998), 41(13):2175-2179.

Yang, et al., "Synthesis and biological activities of potent peptidomimetics selective for somatostatin receptor subtype 2", *Proc. Natl. Acad. Sci. USA* (1998), 95(18):10836-10841.

Yang, L. "Non-peptide Somatostatin Receptor Ligands", *Ann. Rep. Med. Chem.* (Chapter 21) (1999), 34:209-218; Academic Press.

Yang, et al., "2,4-bis (aminomethyl) pyridine derived highly potent and selective human somatostatin receptor subtype-2 (hsst$_2$) agonists", Book of Abstracts, 217th ACS National Meeting, Anaheim, CA, Mar. 21-25, 1999; MEDJ-141.

Yang, et al., "The Design and Synthesis of Non-Peptide Somatostatin Receptor Agonists", Dept. New Millennium, Proc. Am. Pept. Symp., 16th (2000), Meeting date 1999:250-252.

* cited by examiner

NON-PEPTIDE SOMATOSTATIN RECEPTOR LIGANDS

CROSS-REFERENCE TO RELATED APPLICATION

This application claims the benefit of U.S. Provisional Applications, Ser. Nos. 60/344,564 and 60/344,563, both of which were filed Dec. 28, 2001.

BACKGROUND OF THE INVENTION

Somatostatin is an endogenous peptide that performs a variety of important functions within the body. Somatostatin is a highly flexible cyclic peptide with a very short biological half-life. Two known biologically active forms of somatostatin are a 14 mer (SRIF-14) and a 28mer N-terminal extended form (SRIF-28). Naturally-occurring somatostatin (also known as somatotropin release inhibiting factor, SRIF) was originally isolated from ovine hypothalamus.

Somatostatin, originally discovered to act as a classical endocrine hormone of the hypothalamic-pituitary system, has since been shown to act additionally as a paracrine and autocrine signaling factor on a wide variety of cell types. The numerous physiological processes currently recognized to be influenced by somatostatin include hormone and peptide factor secretion, neurotransmission, cell proliferation, smooth muscle contraction, nutrient absorption and inflammation. Hormones and peptides regulated by somatostatin include growth hormone (GH), thyroid-stimulating hormone (TSH), prolactin (PRL), insulin, and substance P (SP).

Somatostatin affects the function of many important biological systems such as the endocrine, gastrointestinal, vascular, and immune systems along with the central and peripheral nervous systems. In the endocrine system, somatostatin plays an important role in controlling growth hormone, insulin and glucagon secretion (Koerker et al., *Science* 1974, 184, 482–484). The effects of somatostatin on the gastrointestinal and vascular biological systems have led to clinical applications for somatostatin therapeutics in both of these areas. In the central nervous system (CNS), somatostatin appears to be an important regulator of cognitive functions (Schettini, *Pharmacological Research* 1991, 23, 203–215) and, in specific areas of the brain, appears to act as a neurotransmitter or as a neuromodulator regulating the release of neurotransmitters such as acetylcholine (Gray et al., *J. of Neuroscience* 1990, 10, 2687–2698) and dopamine (Thal et al., *Brain Research* 1986, 372, 205–209). In the peripheral nervous system (PNS), somatostatin is present in catecholamine containing fibers and in sensory terminals together with substance P (Green et al., *Neuroscience* 1992, 50, 745–749) and acts to inhibit their release and mediated effects.

Somatostatin is expressed in diverse cell types of the immune and hematopoietic systems (Hofland et al., *Ann. Medicine* 1999, 31 Suppl. 2, 23–27) and has been shown to has been demonstrated that somatostatin is important as an endogenous inhibitor of cell proliferation in various normal and neoplastic tissues (Reubi et al., *Trends in Pharmacological Sciences* 1995, 16, 110–115).

The biological effects of somatostatin are mediated through five somatostatin G-protein receptor subtypes, SSTR1-5 (Reisine et al., *Endocrine Reviews* 1995, 16, 427–442), that are highly conserved across different species and can be grouped into two families SSTR 2, 3, and 5, and SSTR 1 and 4. All five receptors are heterogeneously distributed and pharmacologically distinct. Studies utilizing subtype selective somatostatin receptor agonists have provided evidence that somatostatin subtype 2 receptors (SSTR2) mediate the inhibition of growth hormone release from the anterior pituitary and of glucagon release from the pancreas; whereas SSTR5 receptors mediate inhibition of insulin release.

Like somatostatin itself, somatostatin receptors have been localized to a wide variety of tissues and cell types including those belonging to the CNS, PNS, endocrine, gastrointestinal, vascular, and immune systems. A high incidence of somatostatin receptors has also been demonstrated in a variety of human tumors. Neuroendocrine tumors are one class of tumors that exhibit a high density of functionally active somatostatin receptors. Functionally active neuroendocrine tumors present with clinical symptoms such as gastrinoma and glucagonoma syndrome due to excessive hormone release from the tumor cell. Such symptoms may be treated through somatostatin receptor activation.

Another group of tumors recognized as having somatostatin receptors originates in the CNS, which includes both the brain and the spinal cord. While most brain tumors contain somatostatin receptors, their receptor content often varies depending on tumor type. Generally, tumors of glial or meningeal origin, including medulloblastomas, oligodendrogliomas, and differentiated astrocytomas, display somatostatin receptors.

Additional tumors characterized as displaying somatostatin receptors include kidney, breast, and lymphomas, endometrial (Mishima et al., *American Journal of Obstetrics and Gynecology* 1999, 181, 583–590), ovarian (Halmos et al., *Journal of Clinical Endocrinology and Metabolism* 2000, 85, 3509–3512), small cell lung, and prostate (Reubi et al., *Trends in Pharmacological Sciences*, 1995, 16, 110–115).

It has been reported that somatostatin may act directly on cells, e.g., inducing cell death by apoptosis (Srikant, *Biochemical and Biophysical Research Communications* 1995, 209, 400–406). Alternatively, somatostatin may influence tumor growth by indirect mechanisms including effects on growth factor levels that correlate with tumor growth, e.g., IGF-1, or by blocking angiogenesis via inhibiting the proliferation of vascular endothelial cells (Watson et al., *British Journal of Cancer* 2001, 85, 266–272).

Along with somatostatin (SRIF-14) itself, several somatostatin peptide analogs are currently available for various clinical uses. Such uses have been established for cyclic octapeptide therapeutic analogues, including for example, octreotide (Bauer et al., *Life Sciences* 1982, 31,1133), lanreotide (Guisti et al., *European Journal of Clinical Investigation* 1997, 27, 277), and vapreotide (Liebow et al., *Proceedings of the National Academy of Sciences* 1989, 86, 2003). These compounds were originally characterized by their binding effects to prepared rat brain membrane and their effects on endocrine parameters in animals. Structure activity studies on somatostatin peptide analogs have demonstrated that the amino acid side chains from the Phe-Trp-Lys tripeptide subsequence of somatostatin play a key role in receptor binding affinity. The three dimensional structure of octreotide has been determined by x-ray crystallographic studies (see Pohl et al., *Acta Crystallographica* 1995, D51, 48–49). Nuclear magnetic resonance (NMR) structure studies have been performed on other somatostatin peptide analogs (Kessler et al., *Journal of the American Chemical Society* 1983, 105, 6944–6952). These studies indicate that the three dimensional geometry of the amino acid side chains based on the somatostatin Phe-Trp-Lys tripeptide subsequence is defined by a β-turn structure.

Many of the therapeutic properties of somatostatin and somatostatin peptide analogs discussed above can be correlated with the functional activation of the SSTR2 somatostatin receptor subtype as characterized using in vitro cellular constructs which have been transfected with the five individual cloned human somatostatin receptor subtypes.

Current somatostatin peptide therapeutics suffer from numerous drawbacks. Major drawbacks include lack of oral activity, relatively short plasma half life, and poor penetration of the blood retinal barrier (BRB) and of the blood brain barrier (BBB) to access the central nervous system. As a result, somatostatin peptide analog therapeutics are administered to patients in an invasive fashion via injection of an aqueous drug solution up to four times daily, generally by subcutaneous route or by a long acting depot polymer based formulation that is injected every 3–4 weeks with supplemental injections of aqueous drug as needed.

Thus, treatments using currently available somatostatin peptide-based therapeutics lack ease of administration and are not highly selective to specific somatostatin receptor subtypes. Therefore, there exists an unfulfilled need for longer acting, therapeutic non-peptide somatostatin receptor ligands that have greater receptor subtype selectivity, can readily penetrate the BBB and/or the BRB, and can be delivered using non-invasive pharmaceutical methods including oral administration. It is the object of this invention to provide non-peptide somatostatin receptor ligands that meet the unfulfilled needs detailed above.

BRIEF SUMMARY OF THE INVENTION

The subject invention provides non-peptide compounds which are capable of binding to somatostatin receptors. In one embodiment of this invention, these compounds bind to, and activate, a somatostatin receptor. Particularly preferred compounds are those which selectively bind to and activate SSTR2 receptors. The preferred compounds of the subject invention are particularly advantageous because these compounds selectively bind to somatostatin receptors, are stable, are readily administered, and in a specific embodiment, are able to penetrate the BBB and the BRB.

One embodiment of the subject invention provides potent, non-peptide somatostatin receptor ligands based on a central imidazolin-2-one, imidazolin-4-one, or imidazoline-2,4-dione ring as a core heterocyclic scaffolding structure. Appended to the heterocyclic scaffold are three side chains which account for the advantageous activity of the compounds. In a preferred embodiment, at least two groups appended to the core heterocyclic structure contain one or more specific structural elements or substructures that restrict the conformational mobility of these appended groups. In one embodiment, side chains fix this ligand structure in a 3-dimensional geometry that is useful in promoting beneficial biological activity. For example, such ligand structures provided herein elicit biological effects similar to somatostatin upon binding to somatostatin receptors.

Compounds of the present invention may contain one or more asymmetric carbon atoms and may exist in a given diastereomeric, racemic, or enantiomeric form. In the case of the asymmetric carbon atom C5, as labeled in Formulas IA, IB, and IC, it is generally preferred for the somatostatin agonist to have the S-stereochemical assignment. This configuration corresponds to the absolute stereochemistry as derived from L-amino acid derivatives (e.g., L-(+)-tryptophan) as starting materials from which the instant compounds may be prepared. In one embodiment, compounds of the present invention have the S-stereochemical assignment at C5 of Formulas IA, IB, and IC.

In one embodiment of the subject invention, the compounds act as agonists highly specific for the SSTR2 receptor subtype. Also, specifically exemplified herein are somatostatin receptor ligands which are small and exhibit superior penetration of the BBB and BRB. Consequently, the somatostatin receptor ligands of the subject invention are useful for a broad range of therapeutic purposes. These include disorders of the endocrine, gastrointestinal, CNS, PNS, vascular and immune systems as well as cancer.

One category of therapeutic use for the compounds of the subject invention is the treatment of tumors and other forms of cancer. In one embodiment, somatostatin receptor ligands of the present invention can be used to treat solid tumors by efficiently inhibiting angiogenesis. In addition, compounds of the invention retard tumors bearing somatostatin receptors by inhibiting tumor cell growth and proliferation. The ability of compounds of the subject invention to treat various kinds of tumors can be readily confirmed using standard tests including, but not limited to, proliferation tests with various cancer cell lines and tumor growth experiments in nude mice with hormone dependent tumors (see Weckbecker et al., *Cancer Research* 1994, 54: 6334–6337). Thus, the compounds can be used in the treatment of, for example, cancers of the breast, the prostate, the colon, the pancreas, the brain, and the lung.

Another object of the present invention is to provide unique therapeutic compounds that aid in inhibiting gastric, exocrine, and endocrine pancreatic secretion and the release of various peptides of the gastrointestinal tract. These compounds can also be used in the treatment of endocrinological disorders associated with an excess of hormone release, such as growth hormone, glucagon, and insulin.

It is another object of the present invention to provide compounds formulated for oral administration. For example, solutions or suspensions of these compounds may formulated in the form of tablets, capsules (including time release and sustained release formulations), or pills.

Thus, in one embodiment, the present invention provides compounds for use in the treatment of gastro-intestinal (GI) disorders, for example in the treatment of peptic ulcers, disturbances of GI motility, enterocutaneous and pancreaticocutaneous fistula, irritable bowel syndrome, intestinal obstruction, dumping syndrome, watery diarrhea syndrome, acute pancreatitis and gastro-intestinal hormone secreting tumors (e.g., vipomas, glucagonomas, insulinomas, carcinoids and the like).

The present invention also provides novel somatostatin receptor ligands for use in the treatment of multiple sclerosis, pain, anxiety, depression, schizophrenia, neurodegenerative diseases such as Alzheimer's disease and dementia, and epilepsy. In further embodiments, the compounds of the subject invention can be used in the treatment of vascular disorders. Vascular disorders which can be treated include variceal bleeding, and graft vessel diseases such as restenosis or vascular occlusion following vascular insult (e.g., angioplasty, allo- or xenotransplant vasculopathies; graft vessel atherosclerosis, and transplantation of an organ).

Another object of the present invention is to provide compounds useful in the treatment of diabetes and diabetes-related pathologies, including angiopathy, dawn phenomenon, neuropathy, nephropathy, and retinopathy (Grant et al., *Diabetes Care* 2000, 23, 504–509).

Another object of the present invention is to provide the use of novel somatostatin receptor ligand compounds for the manufacture of a medicament for the treatment of conditions as set forth herein.

In still a further object, the invention provides methods for the treatment of the conditions mentioned above, in a patient in need of such treatment, which comprises administering to such patient a therapeutically effective amount of a somatostatin receptor ligand compound of the subject invention.

The present invention provides compounds that may be administered in free form or in pharmaceutically acceptable salt form or complexes. Such salts and complexes may be prepared in a conventional manner and exhibit the activity of the free compounds. A related object of the present invention is to provide pharmaceutical compositions comprising somatostatin receptor ligands in free base form or in pharmaceutically acceptable acid addition salt form in association with a pharmaceutically acceptable diluent or carrier.

DETAILED DESCRIPTION OF THE INVENTION

Figure 1:
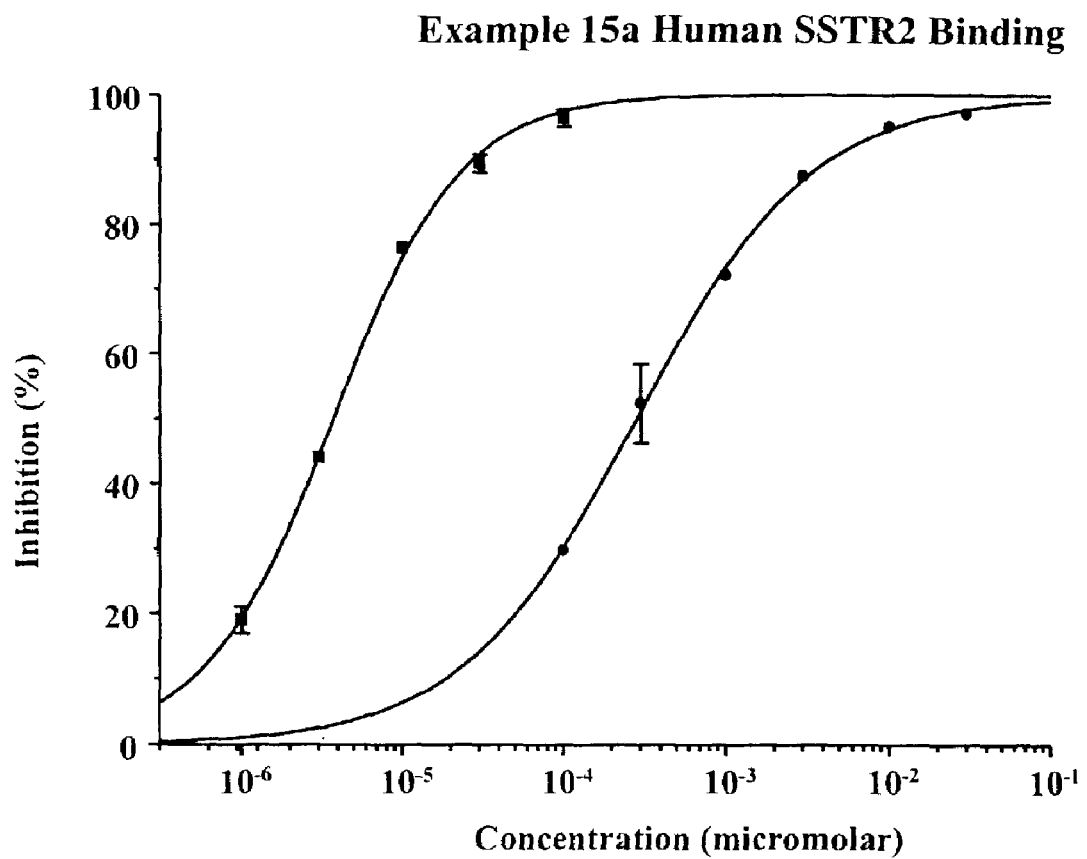
FIG. 1 illustrates the binding affinity of Compound Example 15a to human SSTR2 receptors according to the present invention.

The subject invention provides non-peptide compounds that are capable of binding to somatostatin receptors. In one embodiment of this invention, these compounds bind to, and activate, a somatostatin receptor. Preferred compounds of the subject invention are those compounds which selectively bind to somatostatin receptors, are stable, are readily administered, and in a specific embodiment, are able to penetrate the BBB and the BRB. Particularly preferred compounds are those which selectively bind to and activate somatostatin subtype 2 (SSTR2) receptors. The compounds are useful in the treatment of acromegaly, diarrhea management, diabetic retinopathy, macular degeneration, osteosarcoma, irritable bowel syndrome, and for the treatment of abnormal cellular proliferation, including tumors and cancer, and in particular, neuroendocrine tumors and breast cancer.

In another embodiment, the compounds may treat certain of these disorders through a mechanism that does not involve a somatostatin receptor.

One embodiment of the subject invention provides potent, non-peptide somatostatin receptor ligands based on a central imidazolin-2-one, imidazolin-4-one or imidazoline-2,4-dione ring as a core heterocyclic scaffolding structure. Appended to the heterocyclic scaffold are at least three side chains that account for the advantageous activity of the compounds. In a preferred embodiment, at least two groups appended to the core heterocyclic structure include one or more structural elements that restrict the conformational mobility of these appended groups. This ligand structure fixes side chains in the 3-dimensional geometry necessary for biological activity when bound by a somatostatin receptor. Such ligand structures provided herein elicit biological effects similar to somatostatin upon binding to somatostatin receptors.

In certain embodiments of the subject invention, novel somatostatin receptor ligands of Formula IA are provided as follows:

Formula IA

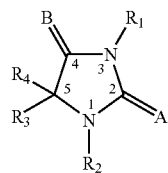

or a pharmaceutically acceptable salt or prodrug thereof, wherein

A and B independently are O or (H, H);

$R_1$ is a group of formula

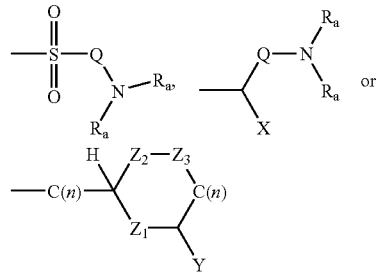

wherein the $R_a$ groups are, independently, hydrogen, alkyl, hydroxyalkyl, alkoxyalkyl, or alkylaryl; X is aryloxy, cyano, —$CO_2R_b$, or —$C(O)N(R_c)_2$ wherein $R_b$ is H, alkyl or alkylaryl and wherein the $R_c$ groups are, independently, hydrogen, alkyl, hydroxyalkyl, alkoxyalkyl, aminoalkyl, alkylaryl, heterocyloalkyl or are optionally joined to form a six membered ring, including for example, morpholine, piperidine, or piperazine ring, optionally substituted with an alkyl group; Q is an alkyl spacer group optionally interrupted by oxygen, sulfur or nitrogen atoms and optionally substituted by hydroxy, alkoxy, alkyl, or aryl; $Z_1$, $Z_2$, and $Z_3$ are, independently, carbon, oxygen, sulfur, or nitrogen optionally substituted with an alkyl; n is an integer from 0 to 2; and Y is either hydrogen, an alkyl, heterocyloalkyl, or $CH_2N(R_a)_2$;

$R_2$ is —$CH(R_d)$—Ar or —$SO_2$—Ar wherein $R_d$ is alkyl, aryl, cyano, —$CO_2R_b$, or —$C(O)N(R_c)_2$; Ar is phenyl or naphthyl optionally and independently, mono- or di-substituted by hydroxy, cyano, halogen, alkyl, alkoxy, —$N(R_a)_2$, alkylthio, alkylsulfonyl, arylsulfonyl, nitro, —$S(O)_2N(R_c)_2$, trifluoromethyl, —$CH_2N(R_a)_2$, —$CO_2R_b$, —$C(O)N(R_c)_2$, or an aromatic group of formula

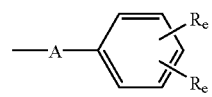

wherein A is $CH_2$, O, NH, S or CO and the $R_e$ groups, independently, are hydrogen, alkyl, alkoxy, trifluoromethyl, cyano, nitro, amino, halogen, hydroxy;

$R_3$ is selected from hydrogen, alkyl, aryl, alkylaryl or heteroaryl; and $R_4$ is a group of formula:

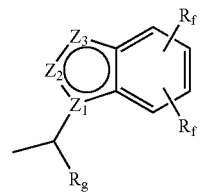

wherein $Z_1$, $Z_2$, and $Z_3$ are, independently, carbon, oxygen, sulfur or nitrogen optionally substituted with an alkyl; $R_f$ is hydrogen, alkyl or an aryl group; and $R_g$ is hydrogen, halogen, cyano, trifluoromethyl, aryl, alkyl or alkoxy.

In a preferred embodiment of Formula IA, A and B are oxygen.

$R_1$ of Formula IA preferably is a group in which 5 or 6 atoms, at least four of which are carbon, separate a basic nitrogen atom from the point of attachment.

$R_2$ of Formula IA preferably is a group of formula —$SO_2$—Ar wherein Ar is an optionally substituted diphenyl ether structure.

$R_3$ of Formula IA preferably is H.

$R_4$ of Formula IA preferably is an optionally substituted 3-indolyl group.

Absolute stereochemistry at C5 of Formula IA preferably is S.

In certain other embodiments of the subject invention, novel somatostatin receptor ligands of Formula IB are provided as follows:

Formula IB or a pharmaceutically acceptable salt or prodrug thereof, wherein

A and B independently are O or (H, H);

$Z_1$, $Z_2$, and $Z_3$ are independently carbon, oxygen, sulfur or a nitrogen atom optionally substituted with an alkyl group;

$R_1$ is a group of formula wherein X is a saturated or unsaturated aliphatic $C_{2-4}$ carbonic chain which is (a) optionally interrupted by —O— or —S— or —N($R_b$)— and/or (b) optionally substituted by hydroxy, alkoxy groups, alkyl, or aryl; and wherein $R_a$ are independently hydrogen, alkyl, or together form a 3–6 carbon-membered ring; and the $R_b$ independently are hydrogen, alkyl, or arylalkyl; and n is an integer from 0 to 2;

$R_2$ is a group of formula —$SO_2$—Ar or —C($R_c$)H—Ar wherein $R_c$ is alkyl, or phenyl optionally substituted by up to three groups alternatively from hydroxy, halogen, alkyl, alkoxy, cyano, trifluoromethyl, amino, monoalkylamino, dialkylamino, carboxy, carboxyalkyl, monoalkylamino-carbonyl, dialkylaminocarbonyl, alkylthio; Ar is phenyl or naphthyl optionally mono- or di-substituted by hydroxy, halogen, alkyl, alkoxy, cyano, trifluoromethyl, aminomethyl, monoalkylaminocarbonyl, dialkylaminocarbonyl, morpholinocarbonyl, piperazinocarbonyl, or a group of formula wherein A is $CH_2$, O, S or CO; $R_d$ independently are hydrogen, alkyl, alkoxy, trifluoromethyl, amino, halogen, or hydroxy;

$R_3$ is hydrogen, alkyl, aryl, heteroaryl or alkylaryl;

$R_4$ is alkyl, aryl, or heteroaryl; and $R_5$ are independently hydrogen, halogen, cyano, alkyl or alkoxyl.

In a preferred embodiment of Formula IB, A and B are O.

$Z_1$ and $Z_2$ of Formula IB are preferably carbon atoms connected by a double bond and $Z_3$ is preferably N—H (e.g., indole).

$R_1$ of Formula IB preferably is a group in which 5 atoms separate a basic nitrogen atom from the point of attachment.

$R_2$ of Formula IB preferably is a group of formula —$SO_2$—Ar wherein Ar is an optionally substituted diphenyl ether structure.

$R_3$ of Formula IB preferably is hydrogen or methyl.

$R_4$ of Formula IB is preferably methyl or substituted phenyl.

$R_5$ of Formula IB is preferably hydrogen, methyl or halogen.

In a preferred embodiment, the subject invention provides novel somatostatin receptor ligands of Formula IC Formula IC or a pharmaceutically acceptable salt or prodrug thereof, wherein:

A and B independently are oxygen, or (H,H);

$R_1$ is a group selected from the following Formula Set A or Formula Set B

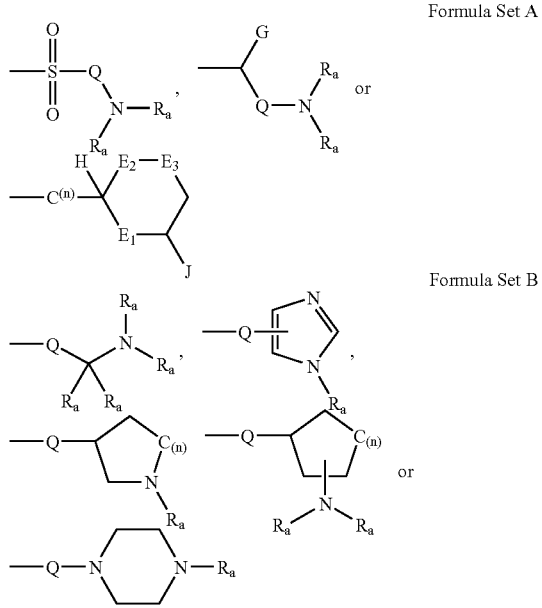

Formula Set A

Formula Set B wherein;
- each $R_a$ independently is hydrogen, alkyl, alkenyl, alkynyl, hydroxyalkyl, alkoxyalkyl, arylalkyl, or form together a 3–6 carbon-membered ring;
- G is aryloxy, cyano, —$CO_2R_a$, or —$C(O)N(R_b)_2$ wherein $R_b$ is independently hydrogen, alkyl, alkenyl, alkynyl, hydroxyalkyl, alkoxyalkyl, monoalkylaminoalkyl, dialkylaminoalkyl, aminoalkyl, arylalkyl, heterocyclylalkyl, or is optionally joined to a five- or six-membered ring, including for example pyrrolidine, morpholine, piperidine, or piperazine ring, optionally substituted with an alkyl group;
- Q is a $C_1$–$C_5$ alkyl, alkenyl, or alkynyl linker group that can optionally include oxygen, sulfur, or nitrogen atoms or —$N(R_a)$— and/or is optionally substituted by hydroxy, alkoxy, alkyl, or aryl;
- each $E_1$, $E_2$, and $E_3$ independently is a carbon, oxygen, sulfur, covalent bond, or nitrogen optionally substituted with an alkyl, alkenyl, alkynyl, alkylaryl, or aryl;
- n is an independently 0, 1, or 2; and
- J is hydrogen, alkyl, heterocyclylalkyl, or $CH_2N(R_a)_2$;
- $R_2$ is —$SO_2$—Ar or $(CHR_c)_n$—Ar
  wherein
  $R_c$ is hydrogen, alkyl, alkenyl, alkynyl, hydroxy, alkoxy, hydroxyalkyl, alkoxyalkyl, aryl, aryloxy, cyano, —$CO_2R_a$ or —$C(O)N(R_b)_2$;
  Ar is phenyl or naphthyl, optionally and independently mono- or di-substituted with hydroxy, cyano, halogen, alkyl, alkenyl, alkynyl, alkoxy, alkylthio, alkylsulfonyl, arylsulfonyl, amino, nitro, trifluoromethyl, aminomethyl, dimethylaminocarbonyl, benzimidazolyloxy, morpholinocarbonyl, or an aromatic group of formula:

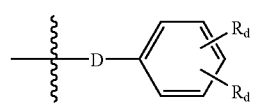

wherein D is oxygen, sulfur, $CH_2$, or CO; and each $R_d$ is independently hydrogen, alkyl, alkenyl, alkynyl, alkoxy; trifluoromethyl, amino, halogen, or hydroxy;
$R_3$ is selected from hydrogen, alkyl, alkenyl, alkynyl, aryl, or heteroaryl; and
$R_4$ is either a group of formula —$CH_2$—Y or $CHR_e$—Y if $R_1$ is a group of Formula Set A or a group of formula $CHR_e$—Y if $R_1$ is a group of Formula Set B;
wherein
$R_e$ is alkyl, alkenyl, alkynyl, hydroxyalkyl, alkoxyalkyl, aminoalkyl, heterocyclylalkyl;
Y is a group of formula

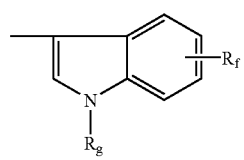

wherein $R_f$ is hydrogen, halogen, or alkoxy; and $R_g$ is hydrogen, alkyl, or benzyl.

In a preferred embodiment of Formula IC, A and B are oxygen.

In one embodiment of Formula IC, A and B are oxygen; $R_1$ preferably is a group of Formula Set A as defined above wherein four to six atoms separate a basic nitrogen atom from the point of attachment at N3 of the heterocyclic core structure of Formula IC; $R_2$ preferably is a group of formula $SO_2$—Ar wherein Ar is an optionally substituted diphenyl ether structure; $R_3$ preferably is hydrogen; and $R_4$ is as defined above wherein $R_e$ preferably is hydrogen, methyl, or substituted phenyl, Y is an optionally substituted indole ring, $R_f$ preferably is hydrogen, methyl, or halogen, and $R_g$ preferably is hydrogen.

In an alternate preferred embodiment of Formula IC, A and B are oxygen; $R_1$ preferably is a group of Formula Set B as defined above wherein four to six atoms separate a basic nitrogen atom from the point of attachment at N3 of the heterocyclic core structure of Formula IC; $R_2$ preferably is a group of formula $SO_2$—Ar wherein Ar is an optionally substituted diphenyl ether structure; $R_3$ preferably is hydrogen or methyl; and $R_4$ is as defined above wherein $R_e$ preferably is methyl or substituted phenyl, Y preferably is an optionally substituted indole ring, $R_f$ preferably is hydrogen, methyl, or halogen, and $R_g$ preferably is hydrogen.

In a further embodiment of Formula IC, various structural elements of the $R_1$–$R_4$ groups restrict the conformational mobility of two or more of the $R_1$–$R_4$ groups appended to the heterocyclic core structure of Formula IC. By restricting the conformation mobility of certain $R_1$–$R_4$ groups, the structure of Formula IC is biased in a desired 3-dimensional geometry which promotes beneficial biological activity and/or potency/selectivity for a given somatostatin receptor subtype. In a preferred embodiment, the structural elements are, independently any of (a), (b) or (c): (a) a group of formula —$SO_2$— (sulfonyl group) attached directly either to the N1 or N3 of the heterocyclic core structure of Formula IC; or (b) a branched group having the structure

wherein each $R_h$ independently is any suitable carbon substituent consistent with the structure for Formula IC (e.g., $C_1$–$C_{10}$ alkyl), and such branched group is attached directly to either N1 or C5 of the heterocyclic core structure of Formula IC; or (c) a 1,3-cis-disubstituted cyclohexyl group embedded within the $R_1$ group appended to N3 of the heterocyclic core structure of Formula IC.

Compounds of the present invention may contain one or more asymmetric carbon atoms and may exist in a given diastereomeric, racemic, or enantiomeric form. In a preferred embodiment, the active compound has an absolute S-stereochemical attachment at C5 of Formulas IA, IB, and IC.

Definitions for Structures of Formula IA and Formula IB

The following definitions are applicable to those structures as defined above for Formula IA and Formula IB.

Unless otherwise specified, as used herein, the term "alkyl" refers to a straight or branched chain alkyl moiety. In one embodiment, the alkyl moiety is $C_{1-8}$ alkyl, which refers to an alkyl moiety having from one to eight carbon atoms, including for example, methyl, ethyl, propyl, isopropyl, butyl, tert-butyl, pentyl, hexyl, and octyl.

The term "alkyl" also includes cycloalkyl, including for example cyclohexyl and the like. The term "alkyl" also includes alkenyl, which refers to a straight or branched alkyl moiety having one or more carbon double bonds, of either E or Z stereochemistry where applicable, and includes for example, vinyl, 1-propenyl, 1- and 2-butenyl, and 2-methyl-2-propenyl.

The term "alkyl" also refers to an alicyclic moiety having from three to six carbon atoms and having in addition one double bond. Such groups, also known as "cycloalkenyl," include, for example, cyclopentenyl and cyclohexenyl.

The term "alkyl" also includes alkynyl moieties, including for example, ethynyl, 1-propynyl, 1- and 2-butynyl, 1-methyl-2-butynyl, and the like.

The term "alkoxy" refers to an alkyl-O-group, in which the alkyl group is as described within this section for the structures of Formula IA and Formula IB.

The term "halogen" is refers to fluorine, chlorine, bromine and iodine.

The term "aryl" refers to an aromatic carbocyclic ring, e.g., phenyl, substituted phenyl and like groups, as well as rings which are fused, e.g., naphthyl, biphenyl indaryl and the like. Aryl groups may be optionally substituted with from 1 to 3 groups of alkyl, aryl, heteroaryl, halogen, hydroxy, alkoxy, nitro, cyano, trifluoromethyl, alkylthio, alkylsulfonyl, arylsulfonyl, $N(R_a)_2$, $S(O)_2N(R_c)_2$, $CH_2N(R_a)_2$, $CO_2R_b$, and $C(O)N(R_c)_2$.

The term "arylalkyl" refers to a moiety in which the "aryl" and "alkyl" groups are as described within this section for the structures of Formula IA and Formula IB.

The term "heterocycloalkyl" refers to a saturated heterocyclic moiety having from two to six carbon atoms and one or more heteroatom from the group N, O, and S (or oxidized versions thereof) which may be optionally benzofused at any available position. This includes, for example, azetidinyl, pyrrolidinyl, tetrahydrofuranyl, piperidinyl, benzodioxolyl and the like.

The term "heterocycloalkyl" also refers to an alicyclic moiety having from three to six carbon atoms and one or more heteroatoms from the group N, O, and S and having in addition one double bond. Such moieties may also be referred to as "heterocycloalkenyl" and includes, for example, dihydropyranyl, and the like.

In the case that the heterocyclyl moiety contains a nitrogen atom that may be substituted, then a substitutent may be chosen from the group of $R_b$.

The term "heteroaryl" refers to monocyclic or bicyclic aromatic ring systems of five to ten atoms of which at least one atom is selected from O, N, and S, in which a carbon or nitrogen atom is the point of attachment, and in which one additional carbon atom is optionally replaced with a heteroatom selected from O or S, and in which from 1 to 3 additional carbon atoms are replaced by nitrogen heteroatoms. The heteroaryl group is optionally substituted with up to three groups selected from alkyl, aryl, heteroaryl, halogen, hydroxy, alkoxy, nitro, cyano, trifluoromethyl, alkylthio, alkylsulfonyl, arylsulfonyl, $N(R_a)_2$, $S(O_2)N(R_c)_2$, $CH_2N(R_a)_2$, $CO_2R_b$, and $C(O)N(R_c)_2$. This term includes, for example, imidazolyl, tetrazolyl, furanyl, thiophenyl, pyridyl, indolyl, quinolyl, benzothiadiazolyl, benzofurazanyl, benzotriazolyl, and the like.

Certain of the above defined terms may occur more than once in Formula IA and/or Formula IB, and upon such occurrence each term shall be defined independently of the other.

The term "orthogonal protecting group" refers to a protecting group which can be removed from a compound while leaving other protecting groups in the compound intact.

Definitions for Structures of Formula IC

The following definitions are applicable to those structures as defined above for Formula IC.

Unless otherwise specified, as used herein, the term "alkyl" refers to a straight, branched chain, or cyclic alkyl moiety containing 1–15 carbon atoms. Preferred straight or branched alkyl groups include methyl, ethyl, propyl, isopropyl, butyl, tert-butyl, pentyl, hexyl, octyl. Preferred cycloalkyl groups include, cyclopentyl and cyclohexyl. The alkyl group specifically includes fluorinated alkyls such as $CF_3$ and other halogenated alkyls such as $CH_2CF_2$, $CF_2CF_3$, the chloro analogs, and the like.

Unless otherwise specified, the term "acyl," as used herein, refers to a group of the formula C(O)R', wherein R' is an alkyl, aryl, arylalkyl group, wherein these groups are as defined within this section for the structures of Formula IC.

The term "alkenyl" refers to a straight or branched alkyl moiety having one or more carbon double bonds, of either E or Z stereochemistry where applicable. This term includes for example, vinyl, 1-propenyl, 1- and 2-butenyl, and 2-methyl-2-propenyl, as well as "cycloalkenyl" groups such as cyclopentenyl and cyclohexenyl.

The term "alkynyl" refers to a straight, branched or cyclic alkyl moiety with at least one triple bond, including but not limited to ethynyl, 1-propynyl, 1- and 2-butynyl, 1-methyl-2-butynyl groups and the like.

The term "alkoxy," as used herein, and unless otherwise specified, refers to a moiety of the structure —O-alkyl, —O-alkenyl, or —O-alkynyl wherein alkyl, alkenyl and alkynyl are as defined above. The alkyl group can be optionally substituted as described above. Alkoxy groups can include methoxy, ethoxy, propoxy, isopropoxy, butoxy, isobutoxy, tertiary butoxy, allyloxy, propargyloxy, $OCF_3$, $OCH_2CF_3$, $OCF_2CF_3$ and the like.

The term "alkylthio," as used herein, refers to an alkyl group attached to the molecule through a sulfur atom.

The term "aryl," as used herein, and unless otherwise specified, refers to either an aromatic carbocyclic ring or rings which are fused including, for example, phenyl, biphenyl, or naphthyl. The aryl group can be optionally substituted with one or more of the moieties selected from the group consisting of alkyl, heteroaryl, heterocyclic, alkoxy, aryloxy, arrylalkoxy; heteroarylalkoxy, carbohydrate, amino acid, amino acid esters, amino acid amides, halo, hydroxyl, carboxyl, acyl, acyloxy, nitro, cyano, thiol, imide, sulfonic acid, sulfate, sulfonyl, sulfanyl, sulfinyl, sulfamoyl, carboxylic ester, carboxylic acid, amide, phosphonyl, phosphinyl, phosphoryl, thioester, thioether, oxime, hydrazine, carbamate, phosphonic acid, phosphate, phosphonate, phosphinate, hydroxamic acid, sulfonylimide, —N($R_a$)$_2$, —N($R_a$)C(O)$R_a$, —N($R_a$)C(O)N($R_a$), —N($R_a$)S(O)$_2R_a$, —S(O)$_2$N($R_a$)$_2$, —CH$_2$N($R_a$)$_2$, —CO$_2R_a$, and —C(O)N($R_a$)$_2$, optionally substituted with, or fused with, an aryl group. This term includes, for example phenyl or naphthyl or any other desired functional group that does not inhibit the pharmacological activity of this compound. Alternatively, adjacent groups on the aryl ring may combine to form a five- to seven-membered carbocyclic, aryl, heteroaryl or heterocylic ring. In another embodiment, the aryl ring is substituted with an optionally substituted cycloalkyl (such as cyclopentyl or cylcohexyl), or an alkylene dioxy moiety (for example methylenedioxy).

The term "arylalkyl," as used herein, and unless otherwise specified, refers to an aryl group as defined above linked to the molecule through an alkyl group as defined above. The aryl portions can be optionally substituted as described within this section for the structures of Formula IC.

The term "aryloxy," as used herein, refers to an aryl or heteroaryl group bound to the molecule through an oxygen atom. The aryl group can be optionally substituted as set out within this section (for the structures of Formula IC) for aryl groups. Preferred aryloxy groups include optionally substituted phenoxy and pyridinyloxy.

The term "halogen" refers to halogen atoms including, for example, fluorine, chlorine, bromine, and iodine.

The terms "heteroaryl" and "heteroaromatic," as used herein, refer to monocyclic or bicyclic aromatic ring systems of five to ten atoms of which at least one atom is selected from O, N, and S, in which a carbon or nitrogen atom is the point of attachment, and in which one additional carbon atom is optionally replaced with a heteroatom selected from O or S, and in which from 1 to 3 additional carbon atoms are replaced by nitrogen heteroatoms. In one embodiment, the heteroaryl group is optionally substituted with up to three groups selected from 1 to 3 of from alkyl, aryl, heteroaryl, heterocyclyl, halogen, hydroxy, alkoxy, nitro, cyano, trifluoromethyl, alkylthio, alkylsulfonyl, arylsulfonyl, —N($R_a$)$_2$, —N($R_a$)C(O)$R_a$, —N($R_a$)C(O)N($R_a$), —N($R_a$)S(O)$_2R_a$, —S(O)$_2$N($R_a$)$_2$, —CH$_2$N($R_a$)$_2$, —CO$_2R_a$, and —C(O)N($R_a$)$_2$, optionally substituted with, or fused with, an aryl group. This term (heteroaryl) includes, for example, phenyl or naphthyl.

Heteroaryl thus includes aromatic and partially aromatic groups which contain one or more heteroatoms. Examples of this type include but are not limited to are furan, benzofuran, thiophene, benzothiophene, pyrrole, pyrazole, imidazole, oxazole, benzoxazole, thiazole, benzthiazole, isothiazole, thiadiazole, triazole, benzotriazole, furazan, benzofurazan, thiafurazan, benzothiafurazan, tetrazole, oxadiazole, triazine, pyridine, pyridazine, pyrimidine, pyrazine, triazine, indolizine, indole, isoindole, purine, quinoline, benzimidazole, pteridine, isoquinoline, cinnoline, quinazoline, quinoxaline, The term "heteroarylalkyl," as used within this section for the structures of Formula IC, refers to a heteroaryl group, as defined above in this section, linked to the molecule through an alkyl group as defined above within this section.

The term "heterocyclyl" and "heterocyclic," as used herein, refers to a nonaromatic cycloalkyl group that may be partially (contains at least one double bond) or fully saturated and wherein one of the carbon atoms in the ring is replaced by a heteroatom, selected from O, S, SO, SO$_2$, or N, and in which up to three additional carbon atoms may be optionally replaced with heteroatoms. Heterocyclic rings are monocyclic, or are fused, bridged, or spiro polycyclic ring systems. Monocyclic heterocyclic rings contain from 3 to 9 member atoms (carbon and heteroatoms), and preferably from 5 to 7 member atoms, in the ring. Polycyclic heterocyclic rings contain from 7 to 12 member atoms in the ring. Preferred polycyclic heterocyclic rings comprise 5-, 6- or 7-membered rings fused to 5-, 6- or 7-membered rings.

Heterocyclyl is linked to a carbon or nitrogen atom. If the heterocyclyl is carbon linked and contains an additional nitrogen, then the additional nitrogen may be substituted by $R_a$. If the heterocyclyl is nitrogen linked and contains an additional nitrogen, then the additional nitrogen may be substituted by $R_a$. Examples of heterocyclyls are piperidinyl, morpholinyl, pyrrolidinyl, tetrahydrofuranyl, dihydrofuranyl, tetrahyropyranyl, dihydropyranyl, imidaolinyl, piperazinyl, pyrolidin-2-onyl, piperidin-2-onyl, succinimidonyl, imidazolidinonyl and the like.

The term "heterocyclylalkyl," as used herein, refers to a heterocyclyl group as defined above linked to the molecule through an alkyl group as defined above.

The term "protected" or "protecting group" as used herein and unless otherwise defined refers to a group that is added to an oxygen, nitrogen, sulfur or phosphorus atom to prevent its further reaction or for other purposes. A wide variety of oxygen and nitrogen protecting groups are known to those skilled in the art of organic synthesis.

General Definitions

The term "mammal" includes humans and all domestic and wild animals including, without limitation, cattle, horses, swine, sheep, goats, dogs, cats, rabbits and the like.

"Optional" or "optionally" means that the subsequently described event, element, or circumstance may or may not occur, and that the description includes instances where said event occurs and instances in which it does not.

The term "enantiomer," as used herein unless otherwise specified, refers to a compound of the present invention having one or more chiral carbon atoms with absolute S or R stereochemical configuration. The term "counter enantiomer" refers to the isomer in which all carbon atoms have the opposite absolute stereochemical configuration. The term "enantiomerically enriched," as used herein, refers to an active compound substantially in the absence of its counter enantiomer. The term "enantiomerically pure," as used herein, refers to a composition having active compounds in excess of 98% absolute stereochemical purity.

Salts encompassed within the terms "pharmaceutically acceptable salts" or "acceptable acid addition salts" refer to non-toxic salts of the compounds of this invention which are generally prepared by reacting the free base with a suitable organic or inorganic acid. Representative salts include, but are not limited to, the following: acetate, benzenesulfonate, benzoate, bicarbonate, bisulfate, bitartrate, borate, camsylate, carbonate, citrate, dihydrochloride, edetate, edisylate, estolate, esylate, fumarate, gluconate, glutamate, hydrobromide, hydrochloride, hydroxynaphthoate, lactate, lactobionate, laurate, malate, maleate, mandelate, mesylate, mucate, napsylate, nitrate, N-methylglucamine ammonium salt, oleate, oxalate, palmoate (embonate), palmitate, pantothenate, phosphate/diphosphate, polygalacturonate, salicylate, stearate, sulfate, subacetate, succinate, tannate, tartrate, tosylate, and valerate.

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or severally.

As used herein, the term "substantially free of" or "substantially in the absence of" or "isolated" refers to a composition that includes at least 95% to 98% by weight, and even more preferably 99% to 100% by weight, of the designated enantiomer of that compound of the present invention. The compounds of the present invention typically have at least one chiral carbon, and therefore, exist as enantiomers. In a preferred embodiment, the active compound is used substantially in the absence of its counter enantiomer.

The term "treatment" as used herein covers any treatment of a disease or disorder in a mammal, particularly a human and includes:

I. Preventing the disease from occurring in a subject which may be predisposed to the disease but has not yet been diagnosed as having it;
II. Inhibiting the disease, e.g., arresting its development; or
III. Relieving the disease, e.g., causing regression of the disease.

Biological Activity and Therapeutic Applications

The somatostatin receptor ligand compounds of the subject invention and their analogs, derivatives, and physiologically acceptable salts, have highly advantageous pharmacological properties. Of particular importance is the ability of these compounds to bind to human somatostatin receptors. In a preferred embodiment, compounds of the subject invention are selective agonists for somatostatin SSTR2 receptors. This activity can be confirmed by, for example, somatostatin receptor binding studies and second messenger functional assays for somatostatin receptors (see Kaupmann et al., FEBS Letters 1993, 331, 53–59). In a preferred embodiment, the compounds of this invention inhibit the binding of somatostatin to its receptor at an $IC_{50}$ of about 100 pM to about 1 μm.

The in vitro biological activity of the compounds of the subject invention can be confirmed in vivo utilizing any of a number of assays well known to those skilled in the art. For example, the compounds can be evaluated for their ability to depress serum GH and insulin levels in the rat. In one example, the test is carried out using male rats. The test substance is administered at varying, logarithmically staggered doses preferably employing at least five (5) rats per dose. One hour after administration of the test substance, blood is taken. The determination of the blood serum GH and insulin levels is measured by radio-immunoassay.

The ability of the compounds of the present invention to act as somatostatin agonists makes them useful as pharmacologic agents for mammals, especially for humans, for the treatment and prevention of disorders wherein somatostatin itself, or the physiological processes it regulates, are involved. These include disorders of the endocrine, gastrointestinal, CNS, PNS, vascular and immune systems as well as cancer.

The somatostatin receptor ligands of the present invention can be used to inhibit various hormone secretions and trophic factors in mammals. Thus, the somatostatin receptor ligands of the subject invention may be administered to treat disorders involving, for example, autocrine or paracrine secretions of trophic factors including cancers of the breast, brain, prostate, and lung (both small cell and non-small cell epidermoids), as well as hepatomas, neuroblastomas, colon and pancreatic adenocarcinomas (ductal type), chondrosarcomas, and melanomas. The compounds of the subject invention can be used to treat SSTR-2 receptor bearing tumors. This activity can be confirmed in proliferation tests with various different cancer cell lines and in tumor growth experiments in nude mice with hormone dependent tumors (see Weckbecker et al., Cancer Research 1994, 54: 6334–6337).

In one embodiment, somatostatin receptor ligands of the present invention promote apoptosis and can be used to treat cancer directly or to sensitize cancer cells for combination treatments using other regimens including radiation therapy or chemotherapy.

Uses of these compounds also include suppressing certain endocrine secretions, such as, insulin, glucagons, prolactin, and GH, which in turn can further suppress the secretion of various trophic factors such as IGF-1. The compounds of the invention are accordingly indicated for use in the treatment of disorders with an etiology comprising or associated with excess GH and trophic factor secretion. The ability to suppress these secretions is useful in the treatment of disorders such as acromegaly. This activity is also useful in the treatment of neuroendocrine tumors, such as carcinoids, vipomas, insulinomas and glucagonomas. The compounds of this invention are also useful for treating diabetes and diabetes-related pathologies, including angiopathy, dawn phenomenon, neuropathy, nephropathy, and retinopathy (Grant et al., Diabetes Care 2000, 23, 504–509).

In another embodiment, compounds of the subject invention can be used to treat vascular disorders including bleeding disorders of the gastrointestinal system, such as those involving the splanchnic blood flow and esophageal varices associated with diseases such as cirrhosis. The ability of the compounds of to mediate vasoconstriction also render them useful in the treatment of cluster headache and migraine.

Compounds of the invention can also be used to inhibit the proliferation of vascular endothelial cells and so are indicated for use in treating graft vessel diseases such as restenosis or vascular occlusion following vascular insult such as angioplasty, allo- or xenotransplant vasculopathies, graft vessel atherosclerosis, and in the transplantation of an organ (e.g., heart, liver, lung, kidney or pancreatic transplants (Weckbecker et al., Transplantation Proceedings 1997, 29, 2599–2600)). Compounds of the invention can also be used to inhibit angiogenesis and are indicated for use in wound healing and treating metastatic stage cancer including but not limited to lung, breast and prostate cancers.

Compounds of the subject invention can also be used for inhibiting gastric and exocrine and endocrine pancreatic secretion and the release of various peptides of the gastrointestinal tract. Thus, these compounds are useful in treating gastro-intestinal disorders, for example in the treatment of peptic ulcers, NSAID-induced ulcers, ulcerative cholitis, acute pancreatitis (e.g., in post-ERCP patients), enterocutancous and pancreaticocutaneous fistula, disturbances of GI motility, intestinal obstruction, chronic atrophic gastritis, non-ulcer dyspepsia, scleroderma, irritable bowel syndrome, Crohn's disease, dumping syndrome, watery diarrhea syndrome, and diarrhea associated such diseases as AIDS or cholera (see O'Dorisio et al., Advances in Endocrinology Metabolism 1990, 1: 175–230).

Somatostatin receptor ligands of the instant invention can also be used in modulating pro-inflammatory mediators such as substance P and various cytokines (Peluso et al., Neuropeptides 1996, 30, 443–451), and maybe used in the therapeutic treatment of psoriasis; arthritis; topical inflammation such as is associated with sunburn, eczema, or other sources of allergies, including asthma; and itching.

In a specific embodiment, the compounds disclosed herein are also functional as neuromodulators in the central nervous system, with useful applications in the treatment of neurodegenerative diseases such as stroke, multiple sclerosis, Alzheimer's disease and other forms of dementia, mental health disorders (such as anxiety, depression, and schizophrenia), and in other neurological diseases such as pain and epilepsy (Vezzani et al., *European Journal of Neuroscience* 1999, 11, 3767–3776).

The instant compounds can also be used in combination with other therapeutic agents. For example, in the case of treating organ transplantation, examples of other therapeutic agents include cyclosporin and FK-506. For treating tumors, examples of other agents include tamoxifen and alpha-interferon. For diabetes, examples of other compounds include metformin or other biguanides, acarbose, sulfonylureas thiazolidinediones or other insulin sensitizers including, but not limited to, compounds which function as agonists on peroxisome proliferator-activated receptor gamma (PPAR-gamma), insulin, insulin-like-growth factor I, glucagon-like peptide I (glp-I) and available satiety-promoting agents such as dexfenfluramine or leptin.

Formulations

Compounds of the present invention may be formulated as solutions or suspensions, in the form of tablets, capsules (each including timed release and sustained release formulations), pills, oils, powders, granules, elixers, tinctures, suspensions, syrups, emulsions, microemulsions, or with excipients. Likewise, they may also be administered by any conventional route, for example in intravenous (both bolus and infusion), intraperitoneal, intraocularly, subcutaneous, intramuscular form, enterally, preferably orally (e.g., in the form of tablets or capsules), or in a nasal, buccal, transdermal, or a suppository form, using well known formulations to those of ordinary skill in the pharmaceutical arts.

In addition, the compounds of the present invention can also be administered in the form of liposomes or the like. Disintegrators include, without limitation, delivery systems such as small unilamellar vesicles, large unilamellar vesicles and multilamellar vesicles. Liposomes can be formed from a variety of phospholipids, such as cholesterol, stearylamine or phosphatidylcholines.

For oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, for example, sodium oleate, sodium stearate, magnesium stearate, sodium benzoate, sodium acetate, sodium chloride, starch, methyl cellulose, agar, bentonite, zanthan gum, and the like.

The somatostatin receptor ligand compounds of the subject invention may be administered as prodrugs in which a group including, for example, esters, peptide amides, or Schiff bases of amines, may be metabolically or spontaneously cleaved upon administration and is fixed to the parent biologically active form of the somatostatin receptor ligand.

The dosage regimen for the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

In general, satisfactory results in animals are indicated to be obtained at a daily dosage of from about 0.1 to about 200 mg, preferably from about 0.1 to about 5 mg/kg animal body weight. In larger mammals, for example humans, an indicated daily dosage is in the range from about 0.5 to about 100 mg, preferably from about 1 to about 50 mg of an agent of the invention conveniently administered, for example, in divided doses up to four times a day or in sustained release form.

Injected intravenous, subcutaneous or intramuscular dosages of the compounds of the present invention, when used for the indicated effects, will range between about 0.001 to 1.0 mg/kg. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration can be continuous rather than intermittent throughout the dosage regimen. Transdermal delivery can also be achieved using approaches known to those skilled in the art.

All patents, patent applications, provisional applications and publications referred to or cited herein are incorporated by reference in their entirety to the extent they are not inconsistent with the explicit teachings of this specification.

Synthetic Procedures

Illustrative examples of procedures which can be used to produce the compounds of the subject invention are outlined below.

List of Abbreviations:
Ac$_2$O— acetic anhydride
Alloc-allyloxycarbonyl
Boc-t-butyloxycarbonyl
Cbz-benzyloxycarbonyl
CDI-N,N'-carbonyldiimidazole
DCC-dicyclohexylcarbodiimide
DCM-dichloromethane
DIEA-diisopropylethylamine
HOBt-hydroxybenztriazole
HPLC-high pressure liquid chromatography
(i-Pr)$_2$NEt-diisopropylethylamine
LHDMS-lithium bis(trimethylsilylamide)
NMR-nuclear magnetic resonance
Ph-phenyl
TBAF-tetrabutyl-ammonium-fluoride
TBDMS-t-butyldimethylsilyl
THF-tetrahydrofuran
THP-tetrahydropyranyl The preparation of compounds of Formula IA, Formula IB, and Formula IC of the present invention may be carried out in sequential or convergent synthetic routes. Compounds with different aromatic or non-aromatic rings and/or bearing additional or different substituents on these rings are readily prepared by minor modification of the methods herein using procedures known in the art.

Conditions used to remove protecting groups such as phenolic benzyl ethers may be changed from catalytic hydrogenation in the presence of a nobel metal such as palladium supported on charcoal to Lewis acid mediated deprotection, e.g., with $BBr_3$, in cases where other functional groups are present, e.g., double bonds and aromatic halogen substituents that are not compatible with catalytic hydrogenation conditions. Synthesis of compounds or intermediates in which multiple amino, hydroxyl and carboxyl group functions require differential protecting group strategies can be carried out by one skilled in the art of organic synthesis by the appropriate selection of orthogonal protecting groups such as benzyl, Cbz, Boc, and Alloc for amino groups and benzyl, methyl, TBDMS, acetyl, THP, for hydroxy groups. Conditions for introducing and removing protecting groups which may be required or present can be found in T. Greene and P. G. M. Wuts, *Protective Groups in Organic Synthesis*, John Wiley & Sons Inc., New York, N. Y. 1991.

Enantiomerically pure or enriched starting materials and intermediates required for the synthesis of enantiomerically pure or enriched compounds of Formulas IA, IB, and IC having defined R or S stereochemistry at C5 and any other given asymmetric carbon atoms may be prepared from enantiomerically pure or enriched α-amino acids or from enantiomerically pure or enriched hydantoins that may in turn be prepared by established literature methods (Duthaler, *Recent Developments in the Stereoselective Synthesis of α-Amino Acids*, Tetrahedron 1994, 50, 1539–1650).

Preparation of Formulas IA IB, and IC

The compounds of Formula IA, IB, and IC maybe prepared as depicted in Scheme I by deprotonating the hydrogen from N1 with a base for a compound of Formula II, wherein A and B are as defined above, wherein the following structure

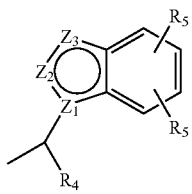

in Formula IB is hereinafter referred to as $R_4$, and wherein $R'_1$, $R'_3$, and $R'_4$ are $R_1$, $R_3$, and $R_4$ as defined above or are optionally protected forms of $R_1$, $R_3$, and $R_4$ thereof. By reacting the resulting anion with a compound of Formula III wherein $R'_2$ is $R_2$ as defined above or is optionally a protected form of $R_2$ and V is a reactive leaving group such as trifluoromethanesulfonate, chlorine, bromine, or iodine, the product is deprotected and a compound of Formulas IA, IB, or IC are recovered in free base or acid addition salt form.

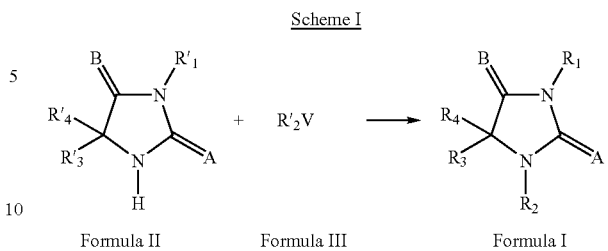

Scheme I

Suitable protecting groups for amino groups of $R'_1$, $R'_2$, $R'_3$ and $R'_4$ include, for example, benzyl, benzyloxycarbonyl, t-butyloxycarbonyl and allyloxycarbonyl. Suitable protecting groups for hydroxy groups of $R'_1$, $R'_2$, $R'_3$ and $R'_4$ include, for example, benzyl, methyl, t-butyldimethylsilyl, acetyl, and tetrahydropyranyl. Suitable groups for carboxy groups of $R'_1$, $R'_2$, $R'_3$ and $R'_4$ include, but are not limited to, benzyl, allyl, methyl, ethyl and t-butyl.

Intermediate compounds of Formula II may be prepared in an enantiomeric, stereochemically homogeneous form according to the following Scheme IIA.

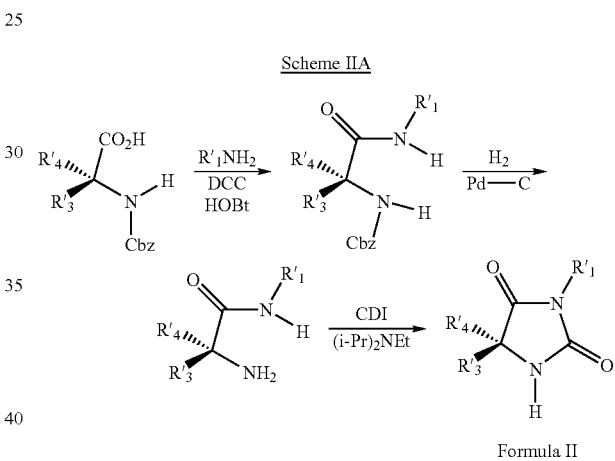

Scheme IIA or in racemic form according to Scheme IIB as described below.

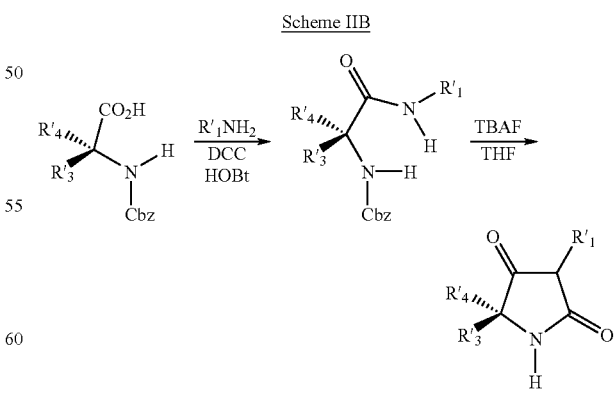

Scheme IIB

In Scheme IIA, the starting material is an enantiomerically pure or enriched N-benzyloxycarbonyl protected α-amino acid, that may be prepared by established methods (e.g., Schotten-Baumann reaction) familiar to those skilled in the art of organic synthesis from an enantiomerically pure α-amino acid (numerous methods for preparing enantiomerically pure α-amino acids are familiar to those skilled in the art of organic synthesis, see e.g., Duthaler, *Tetrahedron* 1994, 50, 1539–1650). This starting material is coupled to a primary amino compound, $R'_1NH_2$, under standard peptide bond formation conditions (e.g., DCC-HOBt), the Cbz protecting group is removed from the condensation product by catalytic hydrogenation and the resulting product is cyclized to form a hydantoin ring using CDI under non-racemizing conditions to yield a product of Formula II having either R or S absolute stereochemical configuration at C5.

In Scheme IIB, the starting material may either be an enantiomerically pure, enantiomerically enriched or a racemic α-N-benzyloxycarbonyl protected α-amino acid, that may be prepared by established methods (e.g., Schotten-Baumann reaction) familiar to those skilled in the art of organic synthesis as described above. This α-N-Cbz-α-amino acid starting material is coupled to a primary amino compound, $R'_1NH_2$, under standard peptide bond formation conditions (DCC-HOBt), and the resulting product is cyclized directly using an excess of TBAF in THF at reflux to yield product of Formula II.

In the case where $R'_3$ is hydrogen, the product of Formula II then represents a mixture of compounds containing equal portions of C5 (R) and C5 (S) stereochemical isomers.

Scheme III depicts a schematic for the synthesis of the unsubstituted diphenylether sulfonyl chlorides: 4-phenoxyphenylsulfonyl chloride. This synthesis schematic is also suitable as a general method for preparing diversely substituted diphenylether sulfonyl chlorides of Formula III to provide substituted sulfonyldiphenylether compositions described in the invention. Compounds of Formula III may be alternatively prepared by other established procedures familiar to those skilled in the art of organic synthesis.

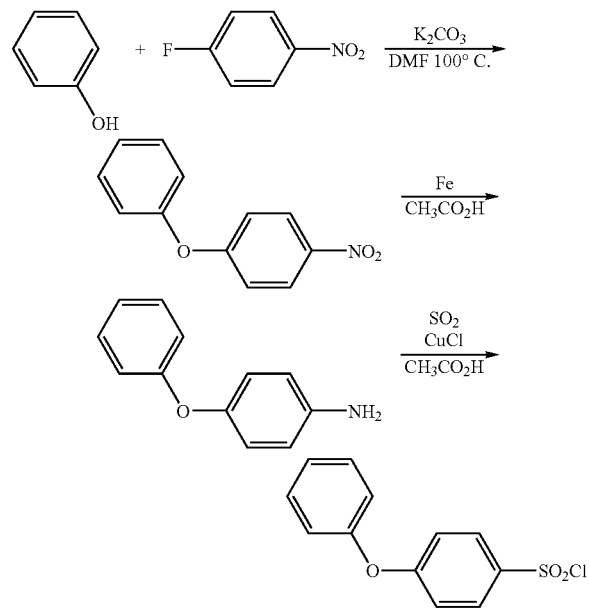

Scheme III

In cases where the primary amine $R'_1NH_2$ contains asymmetric carbon atoms, isomers of absolute R or S stereochemistry may be prepared by standard procedures resulting in compounds of Formulas IA, IB, and IC which are single isomers with homogenous stereochemistry at all asymmetric centers. Likewise, in cases where $R'_2$, $R'_3$, and $R'_4$ groups contain additional asymmetric centers, homogeneous isomers for intermediates containing these groups maybe prepared by literature procedures involving either asymmetric synthesis or standard separation techniques known to one skilled in the art including resolution of chiral addition salts.

General Procedure for Preparation of Compounds of Formula IA, IB, and IC

To a stirred solution of Formula II at a 0.1–1.0M concentration in anhydrous THF is added 1.1 molar equivalents of LHMDS in anhydrous THF at –40° C. under argon. After the addition is complete, a solution of 1.1 molar equivalents of Formula III in THF is added is added and the solution is allowed to warm to room temperature. After stirring for 30 min. at room temperature, saturated ammonium chloride solution is added to neutralize the solution which is then concentrated on a rotary evaporator. Ethyl acetate is added to the mixture followed by extraction with brine, separation and drying the organic phase over sodium sulfate. The organic phase is then concentrated and the resulting crude product is purified by column chromatography over silica gel. The protecting group(s) from the so obtained product is (are) then removed by adding 5 equivalents of $BBr_3$ to a 0.1M solution of the product in dichloromethane at 0° C. (e.g., in the case where $R'_1$, contains a primary amino group protected as N-Boc and $R'_2$ contains a phenolic hydroxy group protected as O—$CH_2Ph$). After stirring for 2 hours at room temperature, potassium bicarbonate is added to yield a neutral mixture from which the organic phase is separated, dried (sodium sulfate) and concentrated to give a crude free base. The crude free base of Formulas IA, IB, or IC is purified by column chromatography over silica gel. The purified free base is then dissolved in ethanolic HCl solution, and this solution is then concentrated to yield the corresponding hydrochloride salt of Formulas IA, IB, and IC.

General Procedure for Preparation of Enantiomerically Pure or Enriched Compounds of Formulas IA, IB and IC An enantiomerically pure or enriched α-N-Cbz-α-amino acid as depicted in Scheme IIA is dissolved with stirring in THF and 1.1 molar equivalents of primary amine intermediate $R'_1$—$NH_2$ is added in THF at room temperature. A 1:1 mixture of DCC:HOBt (1.1 molar equivalents) is then added, and the reaction is stirred until TLC or HPLC analysis indicates that the coupling reaction has proceeded to completion (typically 1–5 hour reaction time). The reaction mixture is then filtered to remove the precipitated dicyclohexylurea, concentrated in vacuo and purified by column chromatography over silica gel. The so obtained product is dissolved in ethanol, along with a catalytic amount a 5% palladium hydrogenation catalyst supported on activated carbon (Pd—C) and the mixture subjected to hydrogenation under an atmosphere of hydrogen. After the uptake of hydrogen by the solution is complete or TLC/HPLC analysis indicates that the reaction is complete, the mixture is filtered and concentrated to yield a crude product which is purified by column chromatography over silica gel or used directly in the subsequent step. To a stirred solution of the hydrogenation product in THF is added a mixture of 1.1 1 molar equivalents of DIEA and 1.1 molar equivalents of CDI at –20° C. The mixture is allowed to stir at 0° C. and then is heated at reflux until TLC/HPLC analysis indicates that the reaction is complete. The reaction mixture is then extracted with saturated ammonium chloride solution, organic phase is dried over sodium sulfate and concentrated to yield the crude product which is purified by column chromatography over silica gel to yield a compound of Formula II.

By was of example, a racemic mixtures of diastereomerically homogeneous compounds of Example 15 (see Table 1 below) can be prepared according to the following general procedures:

Intermediate 1

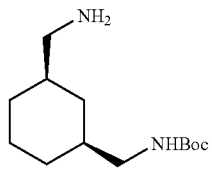

To a stirred solution of racemic cis-1,3-Bis(aminomethyl) cyclohexane (16.1 g, 74.8 mmol,) (*Helv. Chim. Acta* 1979, 62, 1065–1078) in 250 mL methanol, sodium hydroxide (3.11 g, 77.8 mmol,) is added at room temperature. After all the reagents are fully dissolved, di-tert-butyl dicarbonate (6.53 g, 30.0 mmol,), dissolved in 80 mL dioxane, is added dropwise over 1.5 hours. The mixture is stirred at room temperature for 4 hours, filtered and concentrated under reduced pressure. The resulting residue is dissolved in dichloromethane and extracted with aqueous sodium bicarbonate solution. The organic layer is dried over sodium sulfate, filtered and concentrated to give 7.25 g (30.0 mmol) of Intermediate 1 as colorless, viscous oil.

Data regarding the resulting Intermediate 1 are as follows: $^1$H-NMR (CDCl$_3$, 300 MHz): 0.49–0.62 (q, 1H), 0.74–0.90 (m, 2H), 1.20–1.39 (m, 3H), 1.43 (s, 9H), 1.70–1.83 (m, 4H), 2.52 (d, 2H), 2.97 (m, 2H), 3.71 (s, 2H), 4.77 (s, br, 1H).

Intermediate 2

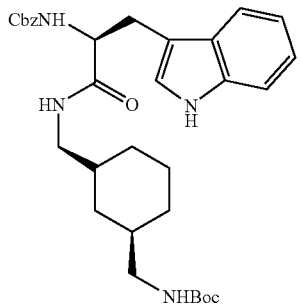
2a

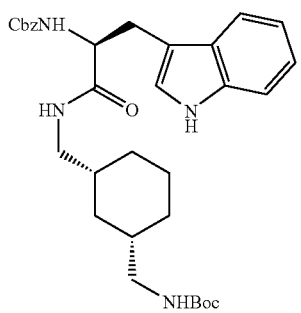
2b

Intermediate 1 (7.25 g, 30.0 mmol,) is then dissolved in 250 mL dichloromethane and then alpha-carbobenzyloxy-L-tryptophan (10.2 g, 30.0 mmol,) and 1-hydroxybenzotriazole (7.28 g, 53.9 mmol) are added to the stirred solution at room temperature under nitrogen. The solution is cooled in an ice bath, and dicyclohexylcarbodiimide (11.1 g, 53.9 mmol,) is added. The reaction mixture is stirred at room temperature overnight, filtered and concentrated to a waxy residue. The waxy residue is triturated with ether/heptane to give 12.5 g (22.2 mmol) of Intermediate 2 as a white powder consisting of an equal mixture of diastercomers 2a and 2b.

Intermediate 3

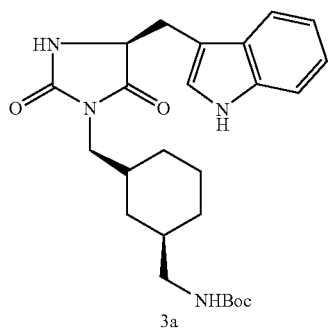
3a

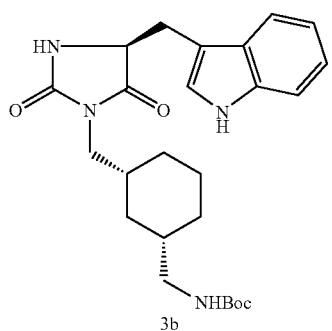
3b

Intermediate 2 (2.81 g, 5.0 mmol,) is dissolved in 55 mL THF and TBAF (15 mmol, 15 mL of a 1.0M solution in THF) is added. The resultant mixture is heated under reflux for 1 hour and concentrated to a residue that is dissolved in ethyl acetate and extracted with brine. The organic layer is dried over sodium sulfate, filtered and concentrated to an oil which is purified by column chromatography over silica gel (chloroform/methanol, 95:5). The fractions containing the product are evaporated and the isomers separated by repeated recrystallization from ethyl acetate/heptane (2:1) to give 1.35 g (2.97 mmol) of one diastereoisomer 3a (illustrated above) as a solid and 0.9 g (1.98 mmol) of the alternative diastereoisomer 3b (illustrated above) as a sticky oil. No definitive relative stereochemical assignment has been made for the respective diastereomers that are depicted in a given form for the sake of convenience.

Data regarding diastereomer 3a are as follows: MS (ESI$^+$) calc. for C$_{25}$H$_{34}$N$_4$O$_4$ 454; Found 455 [M+H]$^+$, $^1$H-NMR (CDCl$_3$, 300 MHz): 0.52–0.75 (m, 2H), 0.98–1.40 (m, 5H), 1.51 (s, 9H), 1.52–1.77 (m, 4H), 1.93 (m, 1H), 2.99–3.53 (m, 3H), 4.28 (m, 2H), 4.87 (t, 1H), 6.40 (s, 1H), 7.00–7.20 (m, 3H), 7.21–7.39 (m, 1H), 7.61 (d, 1H), 10.03 (s, 1H), $^{13}$C-NMR (CDCl$_3$, 75 MHz): 24.8, 26.3, 28.4, 30.3, 33.8, 35.9, 37.3, 44.1, 47.3, 49.1, 57.5, 79.7, 107.1, 111.5, 118.5, 119.2, 121.6, 123.4, 127.7, 136.2, 156.6, 158.2, 174.1.

Data regarding the diastereomer 3b are as follows: $^1$H-NMR (CDCl$_3$, 300 MHz): 0.50–0.72 (m, 2H), 0.83–1.30 (m, 5H), 1.48 (s, 9H), 1.50–1.80 (m, 4H), 2.38 (s, br, 1H) 2.83–3.21 (m, 3H), 4.18 (m, 2H), 4.81 (t, 1H), 6.60 (s, 1H), 7.00–7.18 (m, 3H), 7.21–7.30 (m, 1H), 7.59 (d, 1H), 9.40 (s, 1H), $^{13}$C-NMR (CDCl$_3$, 75 MHz): 24.8, 26.9, 28.3, 30.1, 34.3, 36.3, 37.6, 44.3, 46.8, 57.9, 79.3, 107.9, 111.3, 118.5, 119.2, 121.7, 123.7, 127.2, 136.1, 156.3, 157.9, 174.0.

To a stirred solution of 4-benzyloxy-3-chlorophenol (4.69 g, 20 mmol) in 120 mL DMF, potassium carbonate (4.14 g, 30 mmol), 2-chloro-5-nitro-N,N-dimethylbenzamide (4.57 g, 20 mmol), and 18-crown-6 (0.2 g, 0.75 mmol) are added at room temperature. The mixture is heated at 100° C. for 18 hours, cooled to room temperature, filtered, and concentrated. The resulting residue is dissolved in ethyl acetate and washed with aqueous sodium bicarbonate. The organic layer is concentrated, dissolved in ethanol, stirred with activated charcoal for 15 minutes, filtered, and the solvent evaporated to give 8.2 g (19.2 mmol) of the diphenylether coupling product to be employed for the following reduction step without further purification.

Specifically, the above obtained diphenylether coupling product is dissolved in 100 mL acetic acid/water (1:1) and iron powder (10.76 g, 192 mmol) was added to that solution. The mixture is heated at reflux for 1 hour, cooled to room temperature and 15% sodium hydroxide solution added to adjust the solution to neutral pH. The mixture is filtered and the solid is washed with ethyl acetate. The combined filtrates are washed with water and the organic layer is concentrated and purified by column chromatography over silica gel (ethyl acetate) to give 5.48 g (13.8 mmol) of aniline product as a pale yellow solid.

Intermediate 4

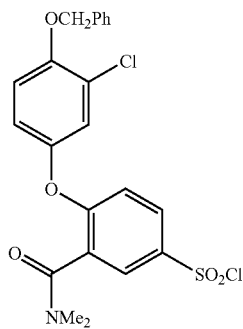

The above obtained 5.48 g of aniline is then dissolved in 50 mL acetic acid containing 5 mL concentrated hydrochloric acid and cooled at –5° C. Sodium nitrite (1.14 g, 16.6 mmol) dissolved in 5 mL water is added dropwise followed by stirring at –5° C. for 1 hour to yield a diazonium salt solution. A separate solution is prepared by adding CuCl$_2$ dihydrate (472 mg, 2.76 mmol) in 1 ml water to 50 mL of SO$_2$-saturated acetic acid. The diazonium salt solution is added to this solution at 0° C. with stirring, and the solution allowed to stand overnight at 4° C. The resulting light green solution is poured into 500 mL ice water and extracted with dichloromethane. The combined organic layers are washed with water, dried over sodium sulfate, and concentrated. The obtained residue is purified by column chromatography over silica gel (ethyl acetate/heptane 2:1) to give 4.71 g (9.82 mmol) of Intermediate 4 as a yellow foam.

Data regarding Intermediate 4 are as follows: MS (ESI$^+$) calc. for C$_{22}$H$_{19}$Cl$_2$NO$_5$S 480; Found 481 [M+H]$^+$, $^1$H-NMR (CDCl$_3$, 300 MHz): 2.98 (s, 3H), 3.11 (s, 3H), 5.19 (s, 2H), 6.86–7.05 (m, 3H), 7.28 (d, 1H), 7.30–7.52 (m, 5H), 7.92 (dd, 1H), 8.04 (d, 1H), $^{13}$C-NMR (CDCl$_3$, 75 MHz): 34.9, 38.3, 71.2, 114.9, 115.8, 119.8, 122.9, 124.4, 127.0, 128.1, 128.2, 128.6, 129.7, 135.9, 137.9, 147.0, 152.2, 159.3, 165.5.

Intermediate 5a

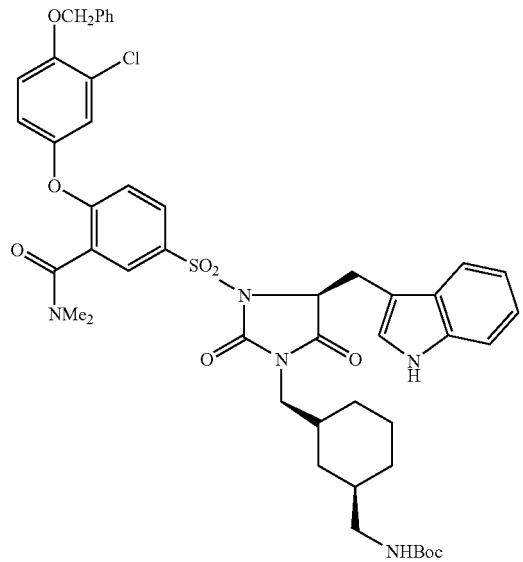

To a stirred solution of Intermediate 3a (454 mg, 1.0 mmol) in 10 mL anhydrous THF, LHMDS (0.9 mmol, 0.9 mL of a 1M solution in hexane) is added at –10° C. under nitrogen. The mixture is stirred at this temperature for 20 minutes, followed by the addition of Intermediate 4 (570 mg, 1.2 mmol) in 5 mL THF. The reaction mixture is allowed to warm to room temperature and is stirred for 1.5 hours. The reaction is quenched by addition of aqueous ammonium chloride solution, concentrated, and partitioned between brine and ethyl acetate. The organic phase was separated, dried over sodium sulfate, filtered, and concentrated to a viscous oil. The oil is purified by column chromatography over silica gel (ethyl acetate/heptane) to give 575 mg (0.64 mmol) of Intermediate 5a as a white foam.

Data regarding Intermediate 5a are as follows: $^1$H-NMR (CDCl$_3$, 300 MHz): 0.20–0.59 (m, 2H), 0.62–1.18 (m, 4H), 1.53 (s, 9H), 1.60 (m, 2H), 2.75 (t, 1H), 2.98 (s, 3H), 3.10 (s, 3H), 3.10 (t, 1H), 3.71 (m, 2H), 4.74 (s, 1H), 4.93 (t, 1H), 5.09 (s, 2H), 6.80 (d, 1H), 6.84–7.50 (m, 12H), 7.69 (m, 1H), 8.01 (m, 2H), 10.06 (s, 1H).

Intermediate 5b

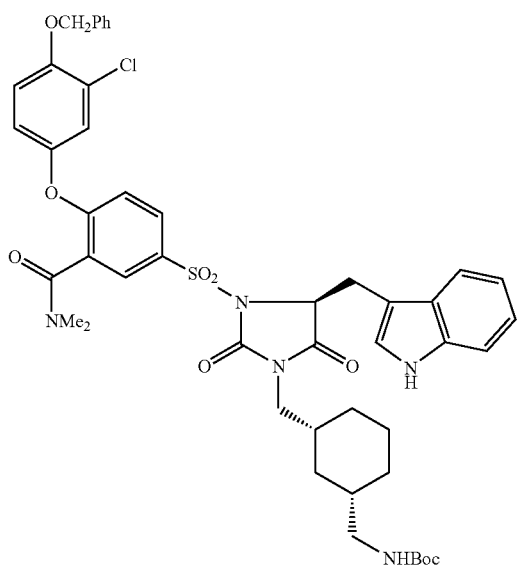

5b

Substituting Intermediate 3b for Intermediate 3a and otherwise following the same procedure used to prepare Intermediate 5a, 396 mg (0.44 mmol) of Intermediate 5b were obtained as a white foam.

Data regarding Intermediate 5b are as follows: $^1$H-NMR (CDCl$_3$, 300 MHz): 0.05–1.35 (m, 6H), 1.48 (m, 4H), 1.68 (s, 9H), 1.70 (m, 2H), 2.90 (m, 1H), 3.09 (m, 1 H), 3.14 (s, 3H), 3.30 (s, 3H), 3.30 (m, 1H), 3.91 (m, 2H), 4.82 (t, 1H), 4.93 (s, 1H), 5.39 (s, 2H), 7.01 (d, 1H), 7.09–7.69 (m, 12H), 7.88 (m, 1H), 8.21 (m, 2H), 9.44 (s, 1H).

Intermediate 6a

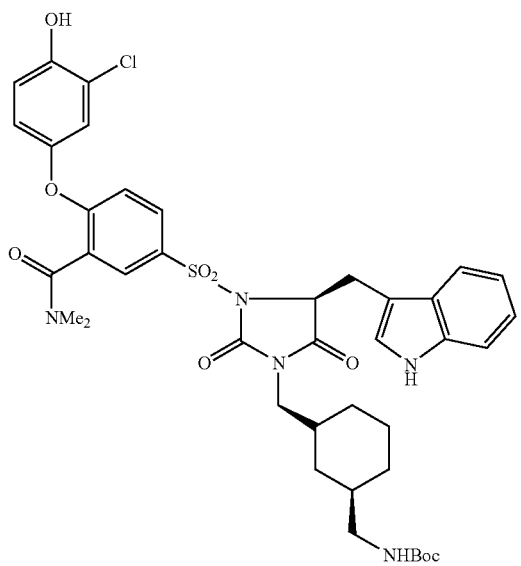

6a

A mixture of Intermediate 5a (494 mg, 0.55 mmol), 49 mg of 10% palladium on carbon, and ammonium formate (346 mg, 5.5 mmol,) in 10 mL of isopropyl acetate/isopropanol (1:1 vv1) containing 50 microliters of concentrated HCl is heated at 85° C. for 1 hour. It is then filtered, the filtrate evaporated, and the residue purified by column chromatography (ethyl acetate/heptane 2:1) to give 399 mg (0.494 mmol, 90%) of Intermediate 6a as a white foam.

Data regarding Intermediate 6a are as follows: $^1$H-NMR (CDCl$_3$, 300 MHz): 0.20–0.59 (m, 3H), 0.62–0.92 (m, 3H), 1.53 (s, 9H), 1.60 (m, 2H), 2.72 (t, 1H), 2.99 (s, 3H), 3.10 (m, 1H), 3.19 (s, 3H), 3.71 (m, 2H), 4.72 (s, 1H), 4.90 (t, 1H), 6.81 (d, 1H) 6.84–7.28 (m, 7H), 7.67 (m, 1H), 8.03 (m, 2H), 10.02 (s, 1H).

Intermediate 6b:

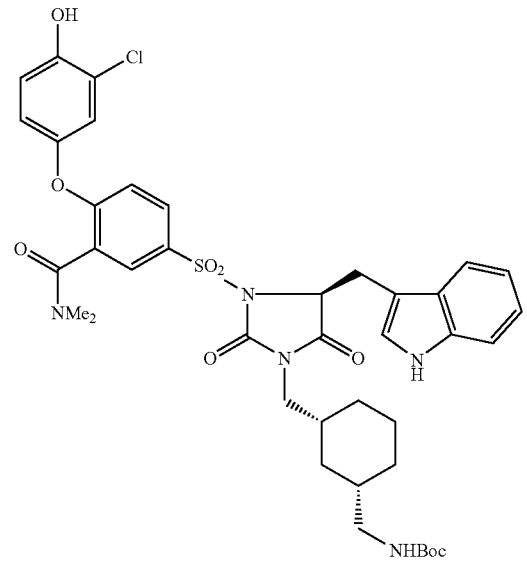

6b

A mixture of Intermediate 5b (670 mg, 0.75 mmol), 67 mg of 10% palladium on carbon, and ammonium formate (470 mg, 7.5 mmol,) in 10 mL of isopropyl acetate/isopropanol (1:1/vv) containing 60 microliters of concentrated HCl is heated at 85° C. for 1 hour. It is then filtered, the filtrate evaporated, and the residue purified by column chromatography (ethyl acetate/heptane 2:1) to give 505 mg (0.63 mmol) of Intermediate 6b as a white foam.

Data regarding Intermediate 6b are as follows: $^1$H-NMR (CDCl$_3$, 300 MHz): 0.06–1.28 (m, 8H), 1.49 (s, 9H), 1.52 (m, 4H), 2.69 (m, 1H), 2.89 (m, 1 H), 2.99 (s, 3H), 3.12 (m, 1H), 3.27 (s, 3H), 3.69 (m, 2H), 4.63 (t, 1H), 4.78 (s, 1H), 6.79–7.30 (m, 8H), 7.67 (m, 1H), 8.01 (m, 2H), 9.22 (s, 1H).

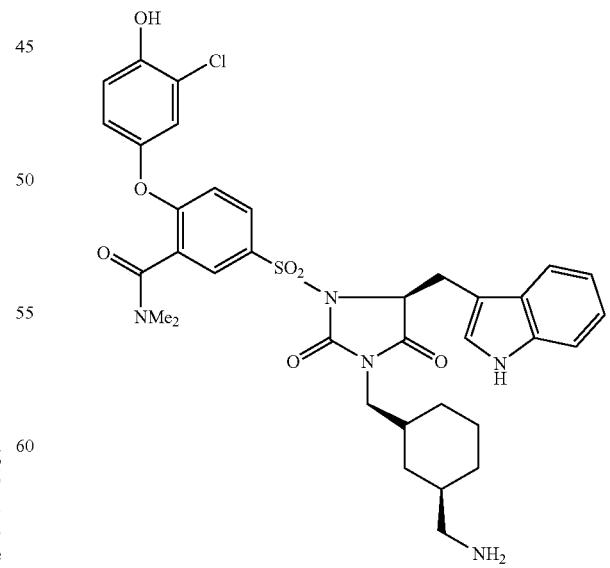

Intermediate 6a (290 mg, 0.36 mmol,) is dissolved in 2 ml of 50% trifluoroacetic acid in dichloromethane. The result ing solution is stirred at room temperature for 1 hour. Sodium bicarbonate is added to adjust the solution to pH 8, and the mixture is partitioned between ethyl acetate and aqueous sodium bicarbonate. The organic layer is dried over sodium sulfate, filtered, and concentrated to a viscous oil. The resulting oil is purified by column chromatography over silica gel (chloroform/methanol/ammonium hydroxide) to give 148 mg (0.21 mmol) of a diastereomer of Compound Example 15 (hereinafter Example 15a, see Table 1 below) in free base form as a white powder. The corresponding hydrochloride salt was prepared by dissolving the free base (148 mg, 0.21 mmol,) in 2 mL 0.2M ethanolic HCl solution, heating the solution at 35° C. for 10 minutes, and then evaporating the solvent. The resulting solid is washed with ether and dried in vacuum to give 126 mg (0.17 mmol) of the hydrochloride salt as a light pink powder.

Data regarding Compound Example 15a are as follows: MS (ESI+) calc. for $C_{35}H_{38}ClN_5O_7S$ 707; Found 708 [M+H]+, $^1$H-NMR (CD$_3$OD, 300 MHz): 0.03–0.13 (m, 1H), 0.16–0.34 (m, 1H), 0.47–0.64 (m, 1H), 0.65–0.76 (m, 1H), 0.83–1.11 (m, 2H), 1.50 (m, 2H), 2.40 (m, 2H), 2.87 (m, 1H), 2.98 (s, 3H), 3.06 (m, 1H), 3.10 (s, 3H), 3.25 (m, 2H), 3.55–3.76 (m, 2H), 4.98 (m, 1H), 6.90–7.17 (m, 7H), 7.32 (d, 1H), 7.61 (d, 1H), 8.09 (m, 2H).

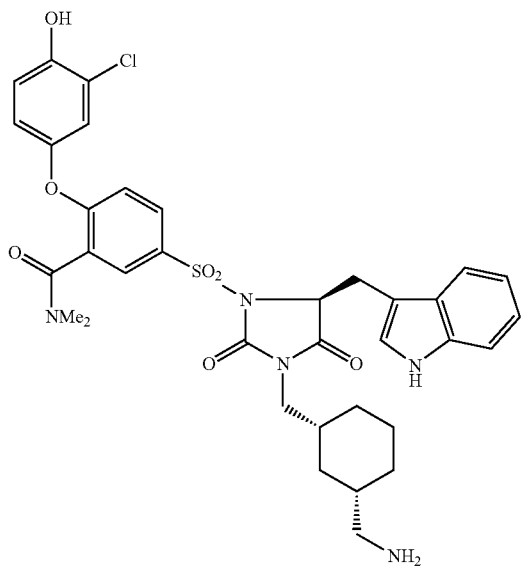

The free base and hydrochloride salt (120 mg, 0.16 mmol) of an alternate diastereomer of Compound Example 15 (hereinafter Example 15b; see Table 1 below) was prepared in analogous fashion to Example 15a above by substituting Intermediate 6b (0.557 mmol, 450 mg) for Intermediate 6a.

Data regarding Compound Example 15b are as follows: MS (ESI+) calc. for $C_{35}H_{38}ClN_5O_7S$ 707; Found 708 [M+H]+, $^1$H-NMR (CD$_3$OD, 300 MHz): 0.10–0.28 (m, 1H), 0.44 (m, 1H), 0.59 (m, 1H), 0.80 (m, 1H), 35 (m, 1H), 1.52 (m, 1H), 2.49 (m, 2H), 2.84 (m, 2H), 2.96 (s, 3H), 3.05 (m, 1H), 3.11 (s, 3H), 3.28 (m, 2H), 3.55–3.74 (m, 2H), 4.97 (m, 1H), 6.90–7.10 (m, 6H), 7.16 (m, 1H), 7.30 (d, 1H), 7.60 (d, 1H), 8.08 (m, 2H).

FIG. 1 illustrates the logarithmic concentration-response curves for inhibition of [$^{125}$I] Somatostatin binding to human SSTR2 receptors expressed in CHO-K1 cells by somatostatin as compared to binding by Compound Example 15a (see Table I) hydrochloride salt. Test compounds were tested in duplicate at all concentrations. The average percent inhibition of duplicate was used for plotting the displacement curves, fitted by non-linear regression. IC$_{50}$ is the concentration of the test substance that causes 50% displacement of [$^{125}$I] somatostatin binding from SSTR2 receptor binding sites. The following Chart I provides the IC$_{50}$ data for both Example 15a HCl salt and somatostatin.

CHART I

| Compound | IC$_{50}$ |
|---|---|
| ● Example 15a HCl salt | 0.290 ± 0.0395 nM |
| ■ Somatostatin | 3.69 ± 0.146 pM |

Figure 2:
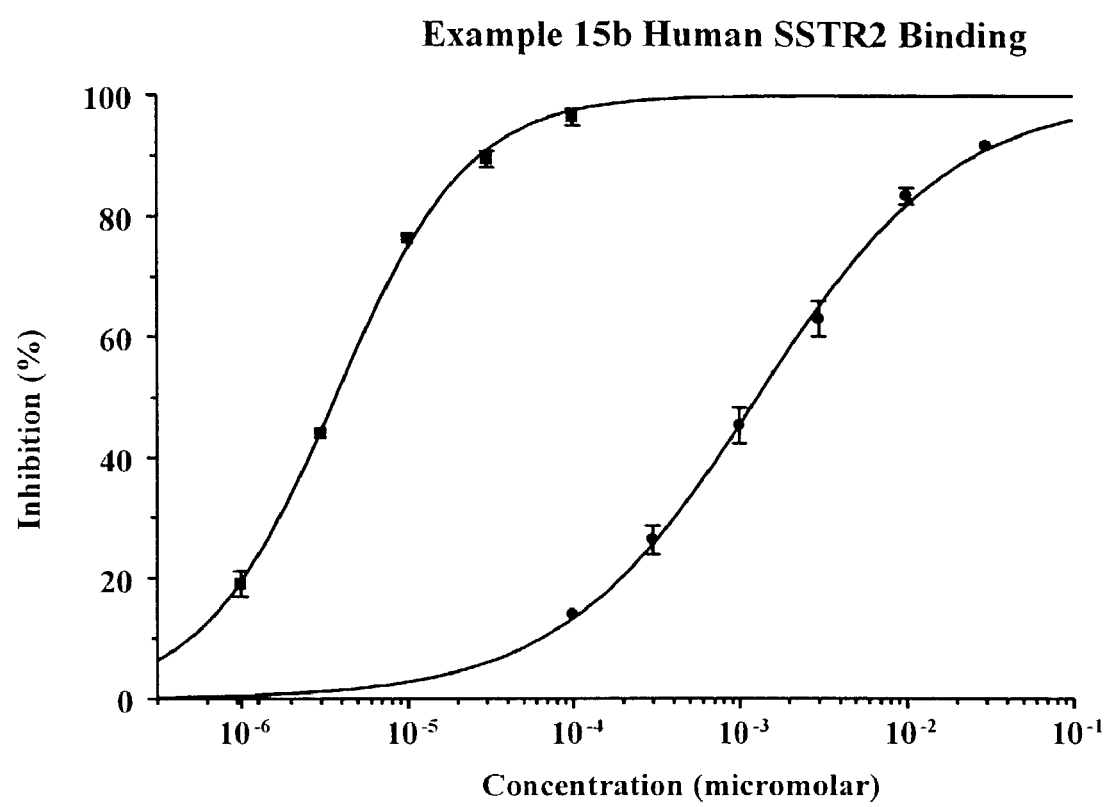
FIG. 2 illustrates the binding affinity of Compound Example 15b to human SSTR2 receptors according to the present invention.

FIG. 2 illustrates the logarithmic concentration-response curves for inhibition of [$^{125}$I] Somatostatin binding to human SSTR2 receptors expressed in CHO-K1 cells by somatostatin and Compound Example 15b (see Table I) hydrochloride salt. Test compounds were tested in duplicate at all concentrations. The average percent inhibition of duplicate was used for plotting the displacement curves, fitted by non-linear regression. IC$_{50}$ is the concentration of the test substance that causes 50% displacement of [$^{125}$I] somatostatin binding from somatostatin SSTR2 receptor binding sites. The following Chart II provides the IC$_{50}$ data for both Example 15a HCl salt and somatostatin.

CHART II

| Compound | IC$_{50}$ |
|---|---|
| ● Example 15b HCl salt | 1.30 ± 0.183 nM |
| ■ Somatostatin | 3.69 ± 0.147 pM |

Examples of compounds of the invention include those defined in the following tables and are prepared in analogous manner to procedures defined above.

TABLE 1

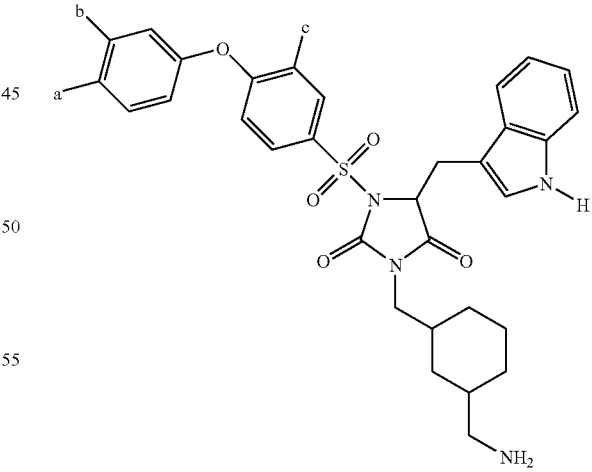

| Example | a | b | c |
|---|---|---|---|
| 1 | OH | H | H |
| 2 | NH$_2$ | H | H |
| 3 | F | H | H |
| 4 | CF$_3$ | H | H |
| 5 | OH | Cl | H |
| 6 | NH$_2$ | Cl | H |

TABLE 1-continued

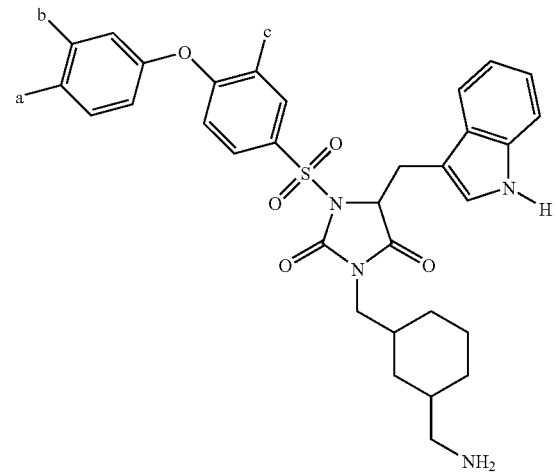

| Example | a | b | c |
|---|---|---|---|
| 7 | F | Cl | H |
| 8 | Cl | Cl | H |
| 9 | OH | H | C(O)N(CH$_3$)$_2$ |
| 10 | NH$_2$ | H | C(O)N(CH$_3$)$_2$ |
| 11 | F | H | C(O)N(CH$_3$)$_2$ |
| 12 | Cl | H | C(O)N(CH$_3$)$_2$ |
| 13 | OCH$_3$ | H | C(O)N(CH$_3$)$_2$ |
| 14 | CF$_3$ | H | C(O)N(CH$_3$)$_2$ |
| 15 | OH | Cl | C(O)N(CH$_3$)$_2$ |
| 16 | NH$_2$ | Cl | C(O)N(CH$_3$)$_2$ |
| 17 | Cl | Cl | C(O)N(CH$_3$)$_2$ |
| 18 | H | Cl | C(O)N(CH$_3$)$_2$ |
| 19 | OCH$_3$ | Cl | C(O)N(CH$_3$)$_2$ |
| 20 | CF$_3$ | Cl | C(O)N(CH$_3$)$_2$ |
| 21 | OH | H | C(O)N(CH$_2$CH$_2$O)$_2$ = morpholine amido |
| 22 | NH$_2$ | H | C(O)N(CH$_2$CH$_2$O)$_2$ |
| 23 | F | H | C(O)N(CH$_2$CH$_2$O)$_2$ |
| 24 | Cl | H | C(O)N(CH$_2$CH$_2$O)$_2$ |
| 25 | OCH$_3$ | H | C(O)N(CH$_2$CH$_2$O)$_2$ |
| 26 | CF$_3$ | H | C(O)N(CH$_2$CH$_2$O)$_2$ |
| 27 | OH | Cl | C(O)N(CH$_2$CH$_2$O)$_2$ |
| 28 | NH$_2$ | Cl | C(O)N(CH$_2$CH$_2$O)$_2$ |
| 29 | Cl | Cl | C(O)N(CH$_2$CH$_2$O)$_2$ |
| 30 | OCH$_3$ | Cl | C(O)N(CH$_2$CH$_2$O)$_2$ |
| 31 | OH | H | CN = cyano |
| 32 | NH$_2$ | H | CN |
| 33 | F | H | CN |
| 34 | Cl | H | CN |
| 35 | OCH$_3$ | H | CN |
| 36 | CF$_3$ | H | CN |
| 37 | OH | Cl | CN |
| 38 | NH$_2$ | Cl | CN |
| 39 | Cl | Cl | CN |
| 40 | OCH$_3$ | Cl | CN |
| 41 | OH | H | Cl |
| 42 | NH$_2$ | H | Cl |
| 43 | F | H | Cl |
| 44 | Cl | H | Cl |
| 45 | OCH$_3$ | H | Cl |
| 46 | CF$_3$ | H | Cl |
| 47 | OH | Cl | Cl |
| 48 | NH$_2$ | Cl | Cl |

TABLE 1-continued

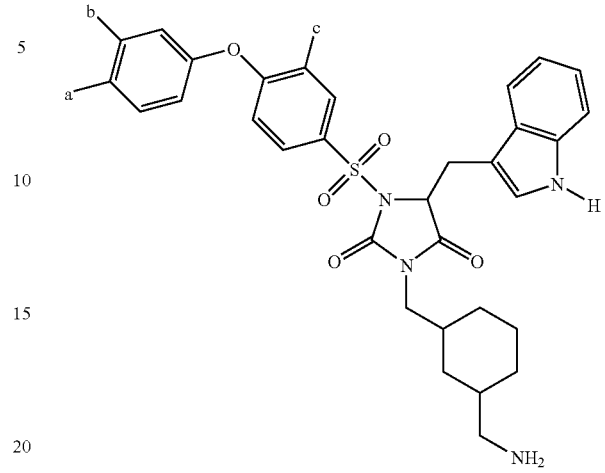

| Example | a | b | c |
|---|---|---|---|
| 49 | Cl | Cl | Cl |
| 50 | OCH$_3$ | Cl | Cl |

TABLE 2

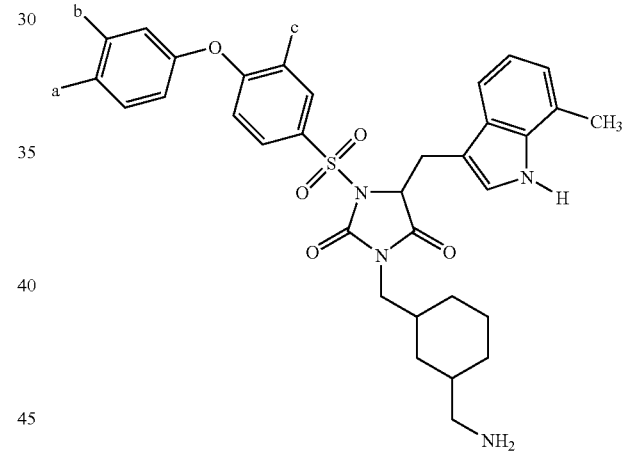

| Example | a | b | c |
|---|---|---|---|
| 51 | OH | H | H |
| 52 | NH$_2$ | H | H |
| 53 | F | H | H |
| 54 | CF$_3$ | H | H |
| 55 | OH | Cl | H |
| 56 | NH$_2$ | Cl | H |
| 57 | F | Cl | H |
| 58 | Cl | Cl | H |
| 59 | OH | H | C(O)N(CH$_3$)$_2$ |
| 60 | NH$_2$ | H | C(O)N(CH$_3$)$_2$ |
| 61 | F | H | C(O)N(CH$_3$)$_2$ |
| 62 | Cl | H | C(O)N(CH$_3$)$_2$ |
| 63 | OCH$_3$ | H | C(O)N(CH$_3$)$_2$ |
| 64 | CF$_3$ | H | C(O)N(CH$_3$)$_2$ |
| 65 | OH | Cl | C(O)N(CH$_3$)$_2$ |
| 66 | NH$_2$ | Cl | C(O)N(CH$_3$)$_2$ |
| 67 | Cl | Cl | C(O)N(CH$_3$)$_2$ |
| 68 | H | Cl | C(O)N(CH$_3$)$_2$ |
| 69 | OCH$_3$ | Cl | C(O)N(CH$_3$)$_2$ |
| 70 | CF$_3$ | Cl | C(O)N(CH$_3$)$_2$ |
| 71 | OH | H | C(O)N(CH$_2$CH$_2$O)$_2$ = morpholine amido |
| 72 | NH$_2$ | H | C(O)N(CH$_2$CH$_2$O)$_2$ |

TABLE 2-continued

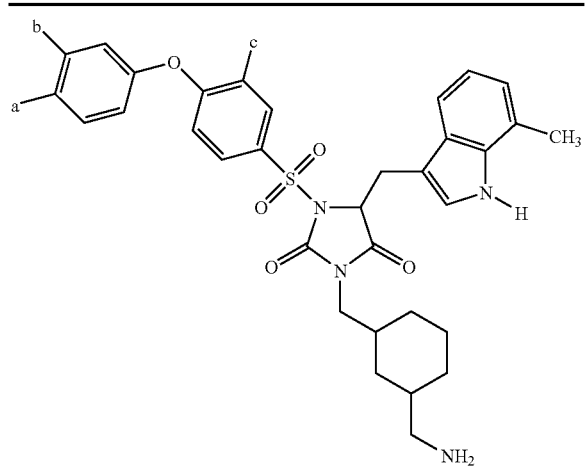

| Example | a | b | c |
|---|---|---|---|
| 73 | F | H | C(O)N(CH$_2$CH$_2$O)$_2$ |
| 74 | Cl | H | C(O)N(CH$_2$CH$_2$O)$_2$ |
| 75 | OCH$_3$ | H | C(O)N(CH$_2$CH$_2$O)$_2$ |
| 76 | CF$_3$ | H | C(O)N(CH$_2$CH$_2$O)$_2$ |
| 77 | OH | Cl | C(O)N(CH$_2$CH$_2$O)$_2$ |
| 78 | NH$_2$ | Cl | C(O)N(CH$_2$CH$_2$O)$_2$ |
| 79 | Cl | Cl | C(O)N(CH$_2$CH$_2$O)$_2$ |
| 80 | OCH$_3$ | Cl | C(O)N(CH$_2$CH$_2$O)$_2$ |

TABLE 3

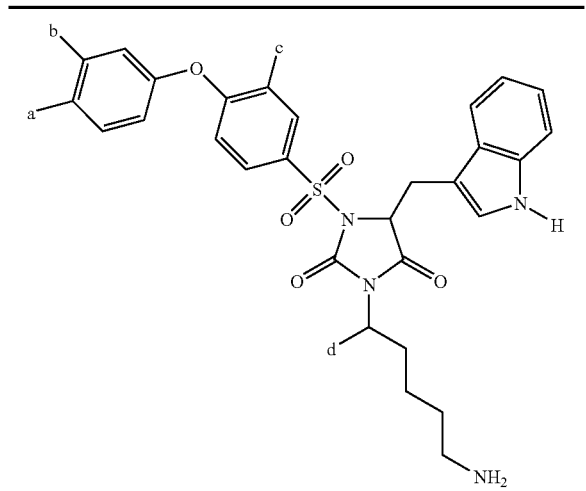

| Example | a | b | c | d |
|---|---|---|---|---|
| 81 | OH | H | H | CO$_2$CH$_3$ |
| 82 | NH$_2$ | H | H | CO$_2$CH$_3$ |
| 83 | OH | Cl | H | CO$_2$CH$_3$ |
| 84 | OH | H | C(O)N(CH$_3$)$_2$ | CO$_2$CH$_3$ |
| 85 | NH$_2$ | H | C(O)N(CH$_3$)$_2$ | CO$_2$CH$_3$ |
| 86 | F | H | C(O)N(CH$_3$)$_2$ | CO$_2$CH$_3$ |
| 87 | OH | Cl | C(O)N(CH$_3$)$_2$ | CO$_2$CH$_3$ |
| 88 | OH | H | C(O)N(CH$_2$CH$_2$O)$_2$ = morpholine amido | CO$_2$CH$_3$ |
| 89 | NH$_2$ | H | C(O)N(CH$_2$CH$_2$O)$_2$ | CO$_2$CH$_3$ |
| 90 | F | H | C(O)N(CH$_2$CH$_2$O)$_2$ | CO$_2$CH$_3$ |
| 91 | OH | Cl | C(O)N(CH$_2$CH$_2$O)$_2$ | CO$_2$CH$_3$ |
| 92 | OH | H | CN = cyano | CO$_2$CH$_3$ |
| 93 | NH$_2$ | H | CN | CO$_2$CH$_3$ |
| 94 | F | H | CN | CO$_2$CH$_3$ |
| 95 | OH | Cl | CN | CO$_2$CH$_3$ |

TABLE 3-continued

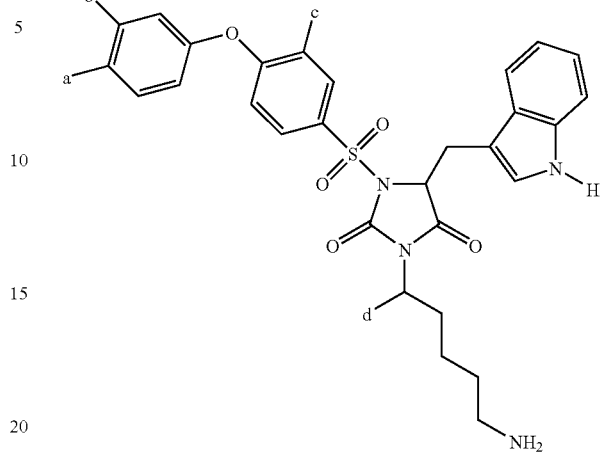

| Example | a | b | c | d |
|---|---|---|---|---|
| 96 | OH | H | Cl | CO$_2$CH$_3$ |
| 97 | NH$_2$ | H | Cl | CO$_2$CH$_3$ |
| 98 | F | H | Cl | CO$_2$CH$_3$ |
| 99 | OH | Cl | Cl | CO$_2$CH$_3$ |
| 100 | OH | H | H | CO$_2$CH$_2$CH$_3$ |
| 101 | NH$_2$ | H | H | CO$_2$CH$_2$CH$_3$ |
| 102 | OH | Cl | H | CO$_2$CH$_2$CH$_3$ |
| 103 | OH | H | C(O)N(CH$_3$)$_2$ | CO$_2$CH$_2$CH$_3$ |
| 104 | NH$_2$ | H | C(O)N(CH$_3$)$_2$ | CO$_2$CH$_2$CH$_3$ |
| 105 | F | H | C(O)N(CH$_3$)$_2$ | CO$_2$CH$_2$CH$_3$ |
| 106 | OH | Cl | C(O)N(CH$_3$)$_2$ | CO$_2$CH$_2$CH$_3$ |
| 107 | OH | H | C(O)N(CH$_2$CH$_2$O)$_2$ = morpholine amido | CO$_2$CH$_2$CH$_3$ |
| 108 | NH$_2$ | H | C(O)N(CH$_2$CH$_2$O)$_2$ | CO$_2$CH$_2$CH$_3$ |
| 109 | F | H | C(O)N(CH$_2$CH$_2$O)$_2$ | CO$_2$CH$_2$CH$_3$ |
| 110 | OH | Cl | C(O)N(CH$_2$CH$_2$O)$_2$ | CO$_2$CH$_2$CH$_3$ |
| 111 | OH | H | CN = cyano | CO$_2$CH$_2$CH$_3$ |
| 112 | NH$_2$ | H | CN | CO$_2$CH$_2$CH$_3$ |
| 113 | F | H | CN | CO$_2$CH$_2$CH$_3$ |
| 114 | OH | Cl | CN | CO$_2$CH$_2$CH$_3$ |
| 115 | OH | H | Cl | CO$_2$CH$_2$CH$_3$ |
| 116 | NH$_2$ | H | Cl | CO$_2$CH$_2$CH$_3$ |
| 117 | F | H | Cl | CO$_2$CH$_2$CH$_3$ |
| 118 | OH | Cl | Cl | CO$_2$CH$_2$CH$_3$ |
| 119 | OH | H | H | CO$_2$-tert-butyl |
| 120 | NH$_2$ | H | H | CO$_2$-tert-butyl |
| 121 | OH | Cl | H | CO$_2$-tert-butyl |
| 122 | OH | H | C(O)N(CH$_3$)$_2$ | CO$_2$-tert-butyl |
| 123 | NH$_2$ | H | C(O)N(CH$_3$)$_2$ | CO$_2$-tert-butyl |
| 124 | F | H | C(O)N(CH$_3$)$_2$ | CO$_2$-tert-butyl |
| 125 | OH | Cl | C(O)N(CH$_3$)$_2$ | CO$_2$-tert-butyl |
| 126 | OH | H | C(O)N(CH$_2$CH$_2$O)$_2$ = morpholine amido | CO$_2$-tert-butyl |
| 127 | NH$_2$ | H | C(O)N(CH$_2$CH$_2$O)$_2$ | CO$_2$-tert-butyl |
| 128 | F | H | C(O)N(CH$_2$CH$_2$O)$_2$ | CO$_2$-tert-butyl |
| 129 | OH | Cl | C(O)N(CH$_2$CH$_2$O)$_2$ | CO$_2$-tert-butyl |
| 130 | OH | H | CN = cyano | CO$_2$-tert-butyl |
| 131 | NH$_2$ | H | CN | CO$_2$-tert-butyl |
| 132 | F | H | CN | CO$_2$-tert-butyl |
| 133 | OH | Cl | CN | CO$_2$-tert-butyl |
| 134 | OH | H | Cl | CO$_2$-tert-butyl |
| 135 | NH$_2$ | H | Cl | CO$_2$-tert-butyl |
| 136 | F | H | Cl | CO$_2$-tert-butyl |
| 137 | OH | Cl | Cl | CO$_2$-tert-butyl |
| 138 | OH | H | H | phenyl |
| 139 | NH$_2$ | H | H | phenyl |
| 140 | OH | Cl | H | phenyl |
| 141 | OH | H | C(O)N(CH$_3$)$_2$ | phenyl |
| 142 | NH$_2$ | H | C(O)N(CH$_3$)$_2$ | phenyl |
| 143 | F | H | C(O)N(CH$_3$)$_2$ | phenyl |

TABLE 3-continued

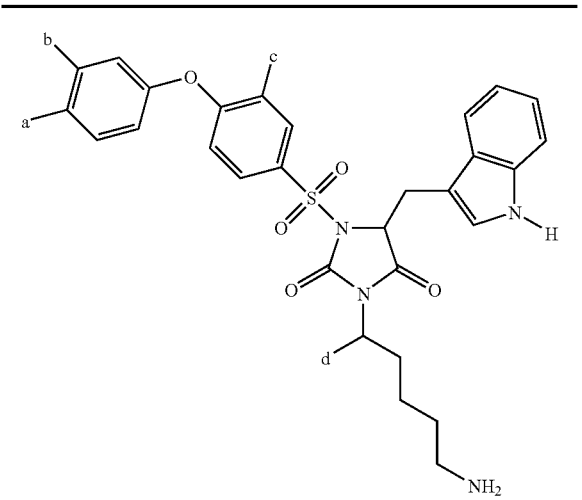

| Example | a | b | c | d |
|---|---|---|---|---|
| 144 | OH | Cl | C(O)N(CH₃)₂ | phenyl |
| 145 | OH | H | C(O)N(CH₂CH₂O)₂ = morpholine amido | phenyl |
| 146 | NH₂ | H | C(O)N(CH₂CH₂O)₂ | phenyl |
| 147 | F | H | C(O)N(CH₂CH₂O)₂ | phenyl |
| 148 | OH | Cl | C(O)N(CH₂CH₂O)₂ | phenyl |
| 149 | OH | H | CN = cyano | phenyl |
| 150 | NH₂ | H | CN | phenyl |
| 151 | F | H | CN | phenyl |
| 152 | OH | Cl | CN | phenyl |
| 153 | OH | H | Cl | phenyl |
| 154 | NH₂ | H | Cl | phenyl |
| 155 | F | H | Cl | phenyl |
| 156 | OH | Cl | Cl | phenyl |
| 157 | OH | H | H | CN = cyano |
| 158 | NH₂ | H | H | CN = cyano |
| 159 | OH | Cl | H | CN = cyano |
| 160 | OH | H | C(O)N(CH₃)₂ | CN = cyano |
| 161 | NH₂ | H | C(O)N(CH₃)₂ | CN = cyano |
| 162 | F | H | C(O)N(CH₃)₂ | CN = cyano |
| 163 | OH | Cl | C(O)N(CH₃)₂ | CN = cyano |
| 164 | OH | H | C(O)N(CH₂CH₂O)₂ = morpholine amido | CN = cyano |
| 165 | NH₂ | H | C(O)N(CH₂CH₂O)₂ | CN = cyano |
| 166 | F | H | C(O)N(CH₂CH₂O)₂ | CN = cyano |
| 167 | OH | Cl | C(O)N(CH₂CH₂O)₂ | CN = cyano |
| 168 | OH | H | CN = cyano | CN = cyano |
| 169 | NH₂ | H | CN | CN = cyano |
| 170 | F | H | CN | CN = cyano |
| 171 | OH | Cl | CN | CN = cyano |
| 172 | OH | H | Cl | CN = cyano |
| 173 | NH₂ | H | Cl | CN = cyano |
| 174 | F | H | Cl | CN = cyano |
| 175 | OH | Cl | Cl | CN = cyano |

TABLE 4

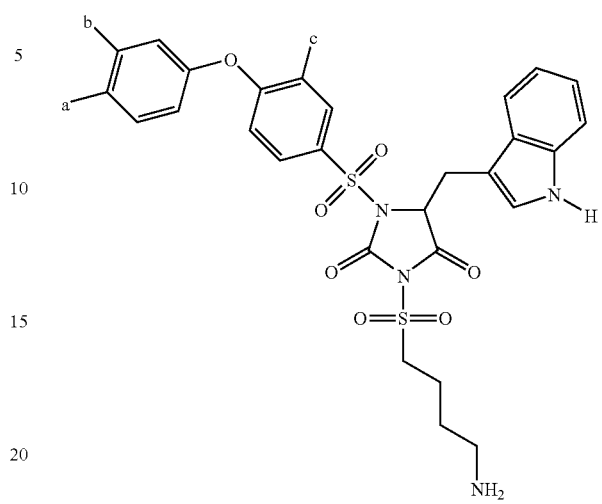

| Example | a | b | c |
|---|---|---|---|
| 176 | OH | H | H |
| 177 | NH₂ | H | H |
| 178 | OH | Cl | H |
| 179 | OH | H | C(O)N(CH₃)₂ |
| 180 | NH₂ | H | C(O)N(CH₃)₂ |
| 181 | F | H | C(O)N(CH₃)₂ |
| 182 | OH | Cl | C(O)N(CH₃)₂ |
| 183 | OH | H | C(O)N(CH₂CH₂O)₂ = morpholine amido |
| 184 | NH₂ | H | C(O)N(CH₂CH₂O)₂ |
| 185 | F | H | C(O)N(CH₂CH₂O)₂ |
| 186 | OH | Cl | C(O)N(CH₂CH₂O)₂ |
| 187 | OH | H | CN = cyano |
| 188 | NH₂ | H | CN |
| 189 | F | H | CN |
| 190 | OH | Cl | CN |
| 191 | OH | H | Cl |
| 192 | NH₂ | H | Cl |
| 193 | F | H | Cl |
| 194 | OH | Cl | Cl |

TABLE 5

| Example | a | b | C | d |
|---|---|---|---|---|
| 195 | OH | H | H | CO₂CH₃ |
| 196 | NH₂ | H | H | CO₂CH₃ |
| 197 | OH | Cl | H | CO₂CH₃ |

TABLE 5-continued

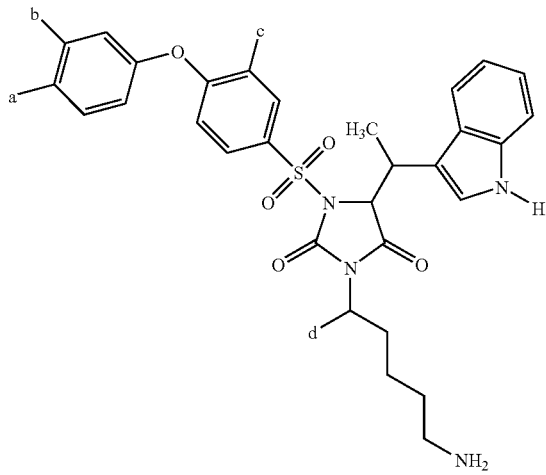

| Example | a | b | C | d |
|---|---|---|---|---|
| 198 | OH | H | C(O)N(CH₃)₂ | CO₂CH₃ |
| 199 | NH₂ | H | C(O)N(CH₃)₂ | CO₂CH₃ |
| 200 | F | H | C(O)N(CH₃)₂ | CO₂CH₃ |
| 201 | OH | Cl | C(O)N(CH₃)₂ | CO₂CH₃ |
| 202 | OH | H | C(O)N(CH₂CH₂O)₂ = morpholine amido | CO₂CH₃ |
| 203 | NH₂ | H | C(O)N(CH₂CH₂O)₂ | CO₂CH₃ |
| 204 | F | H | C(O)N(CH₂CH₂O)₂ | CO₂CH₃ |
| 205 | OH | Cl | C(O)N(CH₂CH₂O)₂ | CO₂CH₃ |
| 206 | OH | H | CN = cyano | CO₂CH₃ |
| 207 | NH₂ | H | CN | CO₂CH₃ |
| 208 | F | H | CN | CO₂CH₃ |
| 209 | OH | Cl | CN | CO₂CH₃ |
| 210 | OH | H | Cl | CO₂CH₃ |
| 211 | NH₂ | H | Cl | CO₂CH₃ |
| 212 | F | H | Cl | CO₂CH₃ |
| 213 | OH | Cl | Cl | CO₂CH₃ |
| 214 | OH | H | H | CO₂CH₂CH₃ |
| 215 | NH₂ | H | H | CO₂CH₂CH₃ |
| 216 | OH | Cl | H | CO₂CH₂CH₃ |
| 217 | OH | H | C(O)N(CH₃)₂ | CO₂CH₂CH₃ |
| 218 | NH₂ | H | C(O)N(CH₃)₂ | CO₂CH₂CH₃ |
| 219 | F | H | C(O)N(CH₃)₂ | CO₂CH₂CH₃ |
| 220 | OH | Cl | C(O)N(CH₃)₂ | CO₂CH₂CH₃ |
| 221 | OH | H | C(O)N(CH₂CH₂O)₂ = morpholine amido | CO₂CH₂CH₃ |
| 222 | NH₂ | H | C(O)N(CH₂CH₂O)₂ | CO₂CH₂CH₃ |
| 223 | F | H | C(O)N(CH₂CH₂O)₂ | CO₂CH₂CH₃ |
| 224 | OH | Cl | C(O)N(CH₂CH₂O)₂ | CO₂CH₂CH₃ |
| 225 | OH | H | CN = cyano | CO₂CH₂CH₃ |
| 226 | NH₂ | H | CN | CO₂CH₂CH₃ |
| 227 | F | H | CN | CO₂CH₂CH₃ |
| 228 | OH | Cl | CN | CO₂CH₂CH₃ |
| 229 | OH | H | Cl | CO₂CH₂CH₃ |
| 230 | NH₂ | H | Cl | CO₂CH₂CH₃ |
| 231 | F | H | Cl | CO₂CH₂CH₃ |
| 232 | OH | Cl | Cl | CO₂CH₂CH₃ |
| 233 | OH | H | H | CO₂-tert-butyl |
| 234 | NH₂ | H | H | CO₂-tert-butyl |
| 235 | OH | Cl | H | CO₂-tert-butyl |
| 236 | OH | H | C(O)N(CH₃)₂ | CO₂-tert-butyl |
| 237 | NH₂ | H | C(O)N(CH₃)₂ | CO₂-tert-butyl |
| 238 | F | H | C(O)N(CH₃)₂ | CO₂-tert-butyl |
| 239 | OH | Cl | C(O)N(CH₃)₂ | CO₂-tert-butyl |
| 240 | OH | H | C(O)N(CH₂CH₂O)₂ = morpholine amido | CO₂-tert-butyl |
| 241 | NH₂ | H | C(O)N(CH₂CH₂O)₂ | CO₂-tert-butyl |
| 242 | F | H | C(O)N(CH₂CH₂O)₂ | CO₂-tert-butyl |
| 243 | OH | Cl | C(O)N(CH₂CH₂O)₂ | CO₂-tert-butyl |
| 244 | OH | H | CN = cyano | CO₂-tert-butyl |
| 245 | NH₂ | H | CN | CO₂-tert-butyl |
| 246 | F | H | CN | CO₂-tert-butyl |
| 247 | OH | Cl | CN | CO₂-tert-butyl |

TABLE 5-continued

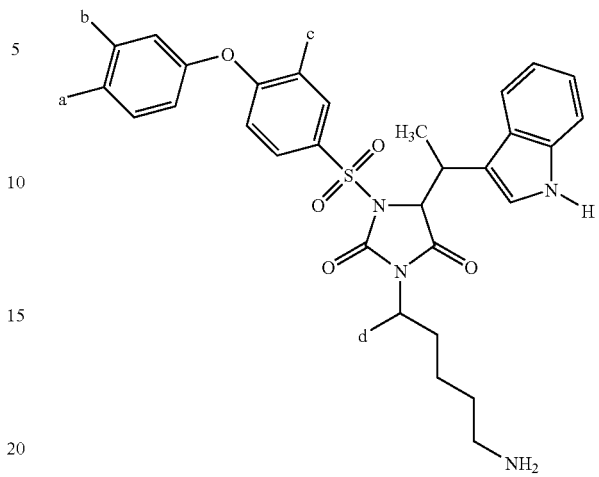

| Example | a | b | C | d |
|---|---|---|---|---|
| 248 | OH | H | Cl | CO₂-tert-butyl |
| 249 | NH₂ | H | Cl | CO₂-tert-butyl |
| 250 | F | H | Cl | CO₂-tert-butyl |
| 251 | OH | Cl | Cl | CO₂-tert-butyl |

TABLE 6

| Example | a | b | c |
|---|---|---|---|
| 252 | OH | H | H |
| 253 | NH₂ | H | H |
| 254 | F | H | H |
| 255 | CF₃ | H | H |
| 256 | OH | Cl | H |
| 257 | NH₂ | Cl | H |
| 258 | F | Cl | H |
| 259 | Cl | Cl | H |
| 260 | OH | H | C(O)N(CH₃)₂ |
| 261 | NH₂ | H | C(O)N(CH₃)₂ |
| 262 | F | H | C(O)N(CH₃)₂ |
| 263 | Cl | H | C(O)N(CH₃)₂ |
| 264 | OCH₃ | H | C(O)N(CH₃)₂ |
| 265 | CF₃ | H | C(O)N(CH₃)₂ |
| 266 | OH | Cl | C(O)N(CH₃)₂ |
| 267 | NH₂ | Cl | C(O)N(CH₃)₂ |
| 268 | Cl | Cl | C(O)N(CH₃)₂ |
| 269 | H | Cl | C(O)N(CH₃)₂ |
| 270 | OCH₃ | Cl | C(O)N(CH₃)₂ |
| 271 | CF₃ | Cl | C(O)N(CH₃)₂ |
| 272 | OH | H | C(O)N(CH₂CH₂O)₂ = morpholine amido |
| 273 | NH₂ | H | C(O)N(CH₂CH₂O)₂ |

TABLE 6-continued

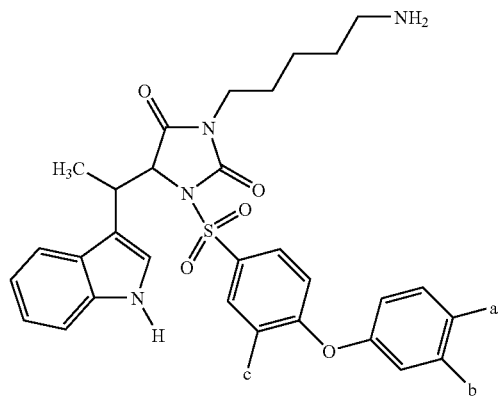

| Example | a | b | c |
|---|---|---|---|
| 274 | F | H | C(O)N(CH₂CH₂O)₂ |
| 275 | Cl | H | C(O)N(CH₂CH₂O)₂ |
| 276 | OCH₃ | H | C(O)N(CH₂CH₂O)₂ |
| 277 | CF₃ | H | C(O)N(CH₂CH₂O)₂ |
| 278 | OH | Cl | C(O)N(CH₂CH₂O)₂ |
| 279 | NH₂ | Cl | C(O)N(CH₂CH₂O)₂ |
| 280 | Cl | Cl | C(O)N(CH₂CH₂O)₂ |
| 281 | OCH₃ | Cl | C(O)N(CH₂CH₂O)₂ |
| 282 | OH | H | CN = cyano |
| 283 | NH₂ | H | CN |
| 284 | F | H | CN |
| 285 | Cl | H | CN |
| 286 | OCH₃ | H | CN |
| 287 | CF₃ | H | CN |
| 288 | OH | Cl | CN |
| 289 | NH₂ | Cl | CN |
| 290 | Cl | Cl | CN |
| 291 | OCH₃ | Cl | CN |
| 292 | OH | H | Cl |
| 293 | NH₂ | H | Cl |
| 294 | F | H | Cl |
| 295 | Cl | H | Cl |
| 296 | OCH₃ | H | Cl |
| 297 | CF₃ | H | Cl |
| 298 | OH | Cl | Cl |
| 299 | NH₂ | Cl | Cl |
| 300 | Cl | Cl | Cl |
| 301 | OCH₃ | Cl | Cl |

TABLE 7

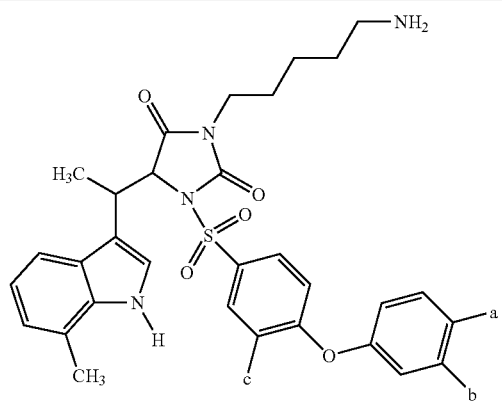

| Example | a | b | C |
|---|---|---|---|
| 302 | OH | H | H |
| 303 | NH₂ | H | H |

TABLE 7-continued

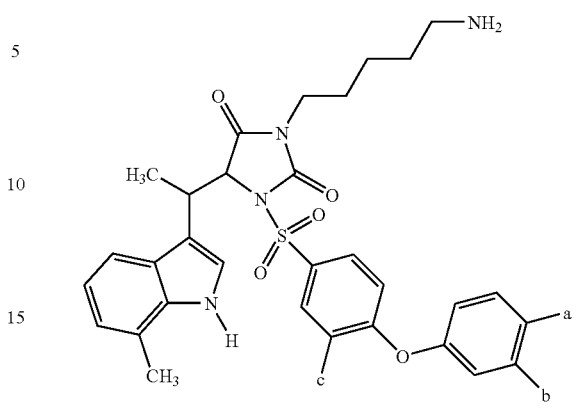

| Example | a | b | C |
|---|---|---|---|
| 304 | F | H | H |
| 305 | CF₃ | H | H |
| 306 | OH | Cl | H |
| 307 | NH₂ | Cl | H |
| 308 | F | Cl | H |
| 309 | Cl | Cl | H |
| 310 | OH | H | C(O)N(CH₃)₂ |
| 311 | NH₂ | H | C(O)N(CH₃)₂ |
| 312 | F | H | C(O)N(CH₃)₂ |
| 313 | Cl | H | C(O)N(CH₃)₂ |
| 314 | OCH₃ | H | C(O)N(CH₃)₂ |
| 315 | CF₃ | H | C(O)N(CH₃)₂ |
| 316 | OH | Cl | C(O)N(CH₃)₂ |
| 317 | NH₂ | Cl | C(O)N(CH₃)₂ |
| 318 | Cl | Cl | C(O)N(CH₃)₂ |
| 319 | H | Cl | C(O)N(CH₃)₂ |
| 320 | OCH₃ | Cl | C(O)N(CH₃)₂ |
| 321 | CF₃ | Cl | C(O)N(CH₃)₂ |
| 322 | OH | H | C(O)N(CH₂CH₂O)₂ = morpholine amido |
| 323 | NH₂ | H | C(O)N(CH₂CH₂O)₂ |
| 324 | F | H | C(O)N(CH₂CH₂O)₂ |
| 325 | Cl | H | C(O)N(CH₂CH₂O)₂ |
| 326 | OCH₃ | H | C(O)N(CH₂CH₂O)₂ |
| 327 | CF₃ | H | C(O)N(CH₂CH₂O)₂ |
| 328 | OH | Cl | C(O)N(CH₂CH₂O)₂ |
| 329 | NH₂ | Cl | C(O)N(CH₂CH₂O)₂ |
| 330 | Cl | Cl | C(O)N(CH₂CH₂O)₂ |
| 331 | OCH₃ | Cl | C(O)N(CH₂CH₂O)₂ |
| 332 | OH | H | CN = cyano |
| 333 | NH₂ | H | CN |
| 334 | F | H | CN |
| 335 | Cl | H | CN |
| 336 | OCH₃ | H | CN |
| 337 | CF₃ | H | CN |
| 338 | OH | Cl | CN |
| 339 | NH₂ | Cl | CN |
| 340 | Cl | Cl | CN |
| 341 | OCH₃ | Cl | CN |
| 342 | OH | H | Cl |
| 343 | NH₂ | H | Cl |
| 344 | F | H | Cl |
| 345 | Cl | H | Cl |
| 346 | OCH₃ | H | Cl |
| 347 | CF₃ | H | Cl |
| 348 | OH | Cl | Cl |
| 349 | NH₂ | Cl | Cl |
| 350 | Cl | Cl | Cl |
| 351 | OCH₃ | Cl | Cl |

TABLE 8

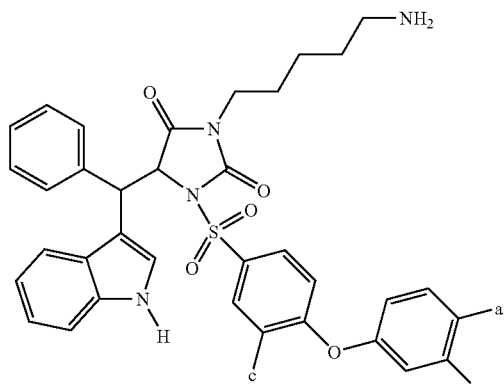

| Example | a | b | c |
|---------|---|---|---|
| 352 | OH | H | H |
| 353 | NH₂ | H | H |
| 354 | F | H | H |
| 355 | CF₃ | H | H |
| 356 | OH | Cl | H |
| 357 | NH₂ | Cl | H |
| 358 | F | Cl | H |
| 359 | Cl | Cl | H |
| 360 | OH | H | C(O)N(CH₃)₂ |
| 361 | NH₂ | H | C(O)N(CH₃)₂ |
| 362 | F | H | C(O)N(CH₃)₂ |
| 363 | Cl | H | C(O)N(CH₃)₂ |
| 364 | OCH₃ | H | C(O)N(CH₃)₂ |
| 365 | CF₃ | H | C(O)N(CH₃)₂ |
| 366 | OH | Cl | C(O)N(CH₃)₂ |
| 367 | NH₂ | Cl | C(O)N(CH₃)₂ |
| 368 | Cl | Cl | C(O)N(CH₃)₂ |
| 369 | H | Cl | C(O)N(CH₃)₂ |
| 370 | OCH₃ | Cl | C(O)N(CH₃)₂ |
| 371 | CF₃ | Cl | C(O)N(CH₃)₂ |
| 372 | OH | H | C(O)N(CH₂CH₂O)₂ = morpholine amido |
| 373 | NH₂ | H | C(O)N(CH₂CH₂O)₂ |
| 374 | F | H | C(O)N(CH₂CH₂O)₂ |
| 375 | Cl | H | C(O)N(CH₂CH₂O)₂ |
| 376 | OCH₃ | H | C(O)N(CH₂CH₂O)₂ |
| 377 | CF₃ | H | C(O)N(CH₂CH₂O)₂ |
| 378 | OH | Cl | C(O)N(CH₂CH₂O)₂ |
| 379 | NH₂ | Cl | C(O)N(CH₂CH₂O)₂ |
| 380 | Cl | Cl | C(O)N(CH₂CH₂O)₂ |
| 381 | OCH₃ | Cl | C(O)N(CH₂CH₂O)₂ |
| 382 | OH | H | CN = cyano |
| 383 | NH₂ | H | CN |
| 384 | F | H | CN |
| 385 | Cl | H | CN |
| 386 | OCH₃ | H | CN |
| 387 | CF₃ | H | CN |
| 388 | OH | Cl | CN |
| 389 | NH₂ | Cl | CN |
| 390 | Cl | Cl | CN |
| 391 | OCH₃ | Cl | CN |
| 392 | OH | H | Cl |
| 393 | NH₂ | H | Cl |
| 394 | F | H | Cl |
| 395 | Cl | H | Cl |
| 396 | OCH₃ | H | Cl |
| 397 | CF₃ | H | Cl |
| 398 | OH | Cl | Cl |
| 399 | NH₂ | Cl | Cl |
| 400 | Cl | Cl | Cl |
| 401 | OCH₃ | Cl | Cl |

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A non-peptide, somatostatin receptor ligand represented by Formula IA:

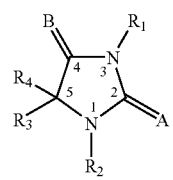

Formula IA wherein

A and B independently are O or (H, H);

$R_1$ is a group of formula

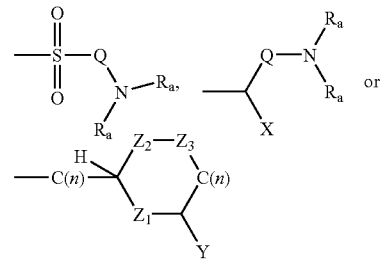

wherein the $R_2$ groups are, independently, hydrogen, alkyl, hydroxyalkyl, alkoxyalkyl, or alkylaryl; X is aryloxy, cyano, —CO₂$R_b$, or —C(O)N($R_c$)₂ wherein $R_b$ is H, alkyl or alkylaryl and wherein the $R_c$ groups are, independently, hydrogen, alkyl, hydroxyalkyl, alkoxyalkyl, aminoalkyl, alkylaryl, heterocyloalkyl or are optionally joined to form a six membered ring; Q is an alkyl spacer group optionally interrupted by oxygen, sulfur or nitrogen atoms and optionally substituted by hydroxy, alkoxy, alkyl, or aryl; $Z_4$, $Z_2$, and $Z_3$ are independently, carbon, oxygen, sulfur, or nitrogen optionally substituted with an alkyl; n is an integer from 0 to 2; and Y is either hydrogen, an alkyl, heterocyloalkyl, or CH₂N($R_a$)₂;

$R_2$ is CH($R_d$)—Ar or —S₂—Ar wherein $R_d$ is alkyl, aryl, cyano, —CO₂$R_b$, or —C(O)N($R_c$)₂; Ar is phenyl or naphthyl optionally and independently, mono- or di-

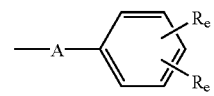

substituted by hydroxy, cyano, halogen, alkyl, alkoxy, —N($R_a$)₂, alkyllhio, alkylsulfonyl, arylsulfonyl, nitro, —S(O)₂N($R_c$)₂, trifluoromethyl, —C₂N($R_a$)₂, —CO₂$R_b$, —C(O)N($R_c$)₂, or an aromatic group of formula wherein A is CH₂, O, NH, S or CO and the $R_c$ groups, independently, are hydrogen, alkyl, alkoxy, trifluoromethyl, cyano, nitro, amino, halogen, hydroxy;

$R_3$ is selected from hydrogen, alkyl, aryl, alkylaryl or heteroaryl; and $R_4$ is a group of formula:

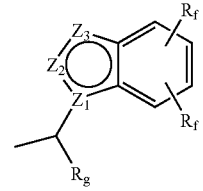

wherein $Z_1$, $Z_2$, and $Z_3$ are, independently, carbon, oxygen, sulfur or nitrogen optionally substituted with an alkyl; $R_f$ is hydrogen, alkyl or an aryl group; and $R_g$ is hydrogen, halogen, cyano, trifluoromethyl, aryl, alkyl or alkoxy.

2. The ligand according to claim 1, wherein A and B are oxygen.

3. The ligand according to claim 1, wherein $R_1$ is a group in which 5 or 6 atoms, at least four of which are carbon, separate a basic nitrogen atom from the point of attachment at N3.

4. The ligand according to claim 1, wherein $R_2$ is a group of formula —$SO_2$—Ar wherein Ar is an optionally substituted diphenyl ether structure.

5. The ligand according to claim 1, wherein $R_3$ is hydrogen.

6. The ligand according to claim 1, wherein $R_4$ is an optionally substituted 3-indolyl group).

7. The ligand according to claim 1, wherein A and B are oxygen, $R_1$ is a group in which 5 or 6 atoms, at least four of which are carbon, separate a basic nitrogen atom from the point of attachment at $N_3$, $R_2$ is —$SO_2$Ar wherein Ar is an optionally substituted diphenyl ether structure, $R_3$ is hydrogen, and $R_4$ is an optionally substituted 3-indolyl group.

8. The ligand according to claim 1, wherein $R_c$ is a morpholine, piperidine, or piperazinc ring, optionally substituted with an alkyl group.

9. The ligand according to claim 1, wherein the structure of Formula IA contains one or more asymmetric carbon atoms.

10. The ligand according to claim 9, in diastereomeric, racemic, or enantiomeric form.

11. The ligand according to claim 10, having an absolute S-stereochemical configuration at C5.

12. A pharmaceutical composition comprising a compound according to claim 1 and a pharmaceutically acceptable carrier or diluent.

13. The pharmaceuticaly composition according to claim 12, in free base or pharmaceutically acceptable acid addition salt form.

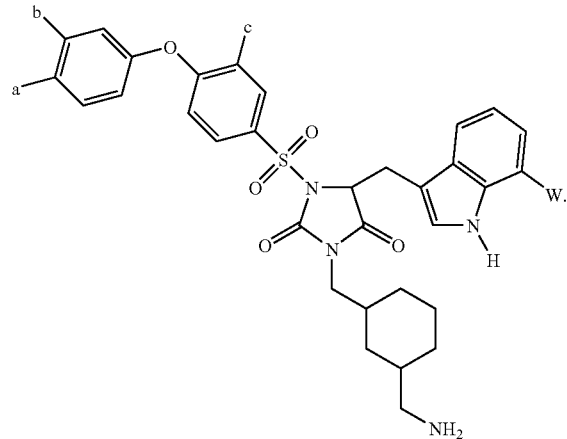

14. The ligand according to claim 1, wherein the ligand has the following structure
wherein
a is H, OH, $NH_2$, F, $CF_3$, Cl, or $OCH_3$;
b is H or Cl;
c is H, $C(O)N(CH_3)_2$, $C(O)N(CH_2CH_2O)_2$, CN, or Cl; and
W is H or $CH_3$.

15. The ligand according to claim 1, wherein the ligand has the

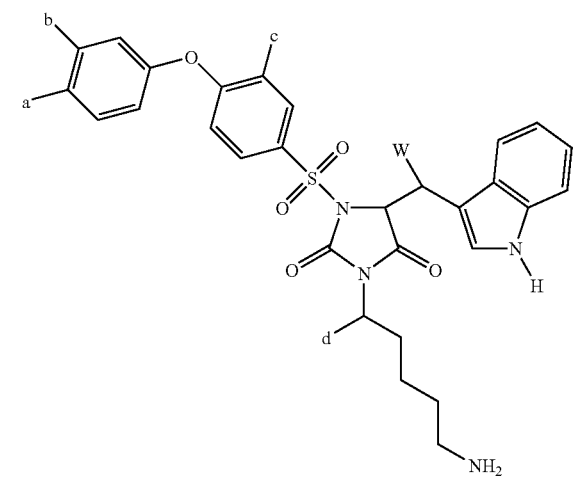

following structure
wherein
a is OH, $NH_2$, or F;
b is H or Cl;
c is H, $C(O)N(CH_3)_2$, $C(O)N(CH_2CH_2O)_2$, CN, Cl, or H;
d is $CO_2CH_3$, $CO_2CH_2CH_3$, $CO_2$-tert-butyl, phenyl, CN, and
W is H or $CH_3$.

16. The ligand according to claim 1, wherein the ligand has the

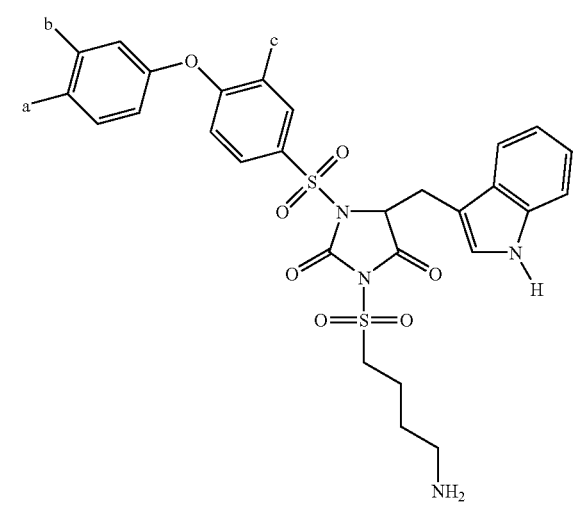

following structure
wherein
a is OH, $NH_2$, or F;
b is H or Cl; and
c is H, $C(O)N(CH_3)_2$, $C(O)N(CH_2CH_2O)_2$, CN, or Cl.

17. A process for the preparation of a compound of Formula IA as defined in

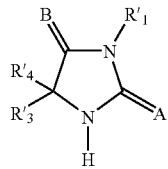

Formula II claim 1, which includes the steps of reacting a compound of Formula II wherein A and B are as defined in claim 1 and $R'_1$, $R'_3$, and $R'_4$ are $R_1$, $R_3$, and $R_4$ as defined in claim 1 or protected forms of $R_1$, $R_3$, and $R_4$, with a compound of Formula III $$R'_2V$$

Formula III wherein $R'_2$ is $R_2$ as defined in claim 1 or is a protected form of $R_2$ and V is a reactive leaving group, deprotecting the resulting product and recovering the thus obtained compound of Formula IA in free base or acid addition salt form.

18. The process according to claim 17, wherein V is trifluoromethanesulfonate, chlorine, bromine, or iodine.

* * * * *

UNITED STATES PATENT AND TRADEMARK OFFICE
CERTIFICATE OF CORRECTION

| | | |
|---|---|---|
| PATENT NO. | : 7,189,856 B2 | Page 1 of 3 |
| APPLICATION NO. | : 10/289924 | |
| DATED | : March 13, 2007 | |
| INVENTOR(S) | : Gideon Shapiro et al. | |

It is certified that error appears in the above-identified patent and that said Letters Patent is hereby corrected as shown below:

Column 1,
Lines 57-58, "and has been shown to has been demonstrated" should read --and has been shown to inhibit cytokine secretion (*e.g.*, IL-1β) from peripheral blood mononuclear cells (Peluso *et al.*, *Neuropeptides* 1996, 30, 443-451) and inhibit the production of immunoglobulin (Ig)E from B lymphocytes (Kimata *et al.*, *J. Immunology* 1993, 150, 4630-4640). Furthermore, it has been demonstrated--.

Column 16,
Line 61, "enterocutancous" should read --enterocutaneous--.

Column 20,
Lines 56-63, 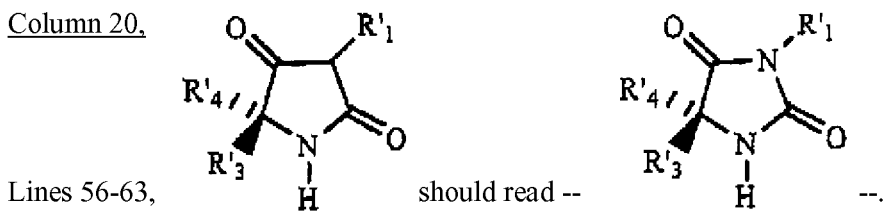 --.

Column 42,
Line 41, "-S$_2$-Ar wherein" should read -- -SO$_2$-Ar wherein--.
Lines 42-53, "Ar is phenyl or naphthyl optionally and independently, mono- or di-

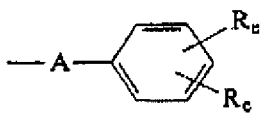

substituted by hydroxy, cyano, halogen, alkyl, alkoxy, -N(R$_a$)$_2$, alkyllthio, alkylsulfonyl, arylsulfonyl, nitro, -S(O)$_2$N(R$_c$)$_2$, trifluoromethyl, -C$_2$N(R$_a$)$_2$, -CO$_2$R$_b$, -C(O)N(R$_c$)$_2$, or an aromatic group of formula wherein A is CH$_2$, O, NH, S or CO and the R$_c$ groups"

should read

-- Ar is phenyl or naphthyl optionally and independently, mono- or di-substituted by hydroxy, cyano, halogen, alkyl, alkoxy, -N(R$_a$)$_2$, alkylthio, alkylsulfonyl, arylsulfonyl, nitro, -S(O)$_2$N(R$_c$)$_2$, trifluoromethyl, -CH$_2$N(R$_a$)$_2$, -CO$_2$R$_b$, -C(O)N(R$_c$)$_2$, or an aromatic group of formula

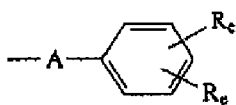

wherein A is CH$_2$, O, NH, S or CO and the R$_e$ groups--.

UNITED STATES PATENT AND TRADEMARK OFFICE
CERTIFICATE OF CORRECTION

PATENT NO. : 7,189,856 B2
APPLICATION NO. : 10/289924
DATED : March 13, 2007
INVENTOR(S) : Gideon Shapiro et al.

It is certified that error appears in the above-identified patent and that said Letters Patent is hereby corrected as shown below:

Column 43,
Lines 41-57,
"wherein the ligand has the following structure wherein"

should read

--wherein the ligand has the following structure

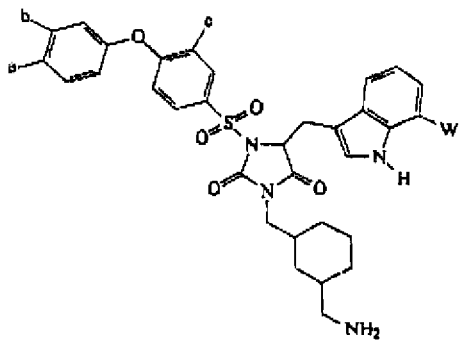

wherein--.

Column 44,
Lines 1 -26,
"wherein the ligand has the         should read        --wherein the ligand has the
                                                        following structure

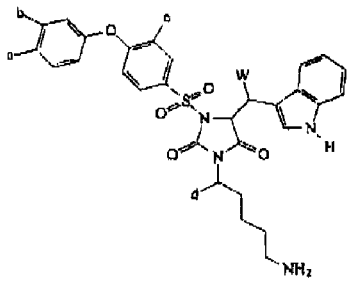                                    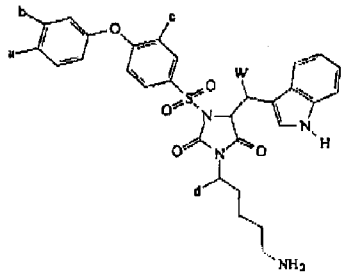

following structure wherein"                             wherein--.

UNITED STATES PATENT AND TRADEMARK OFFICE
CERTIFICATE OF CORRECTION

PATENT NO. : 7,189,856 B2  Page 3 of 3
APPLICATION NO. : 10/289924
DATED : March 13, 2007
INVENTOR(S) : Gideon Shapiro et al.

It is certified that error appears in the above-identified patent and that said Letters Patent is hereby corrected as shown below:

Column 44.
Lines 35-63,
"wherein the ligand has the     should read     --wherein the ligand has the
                                                following structure

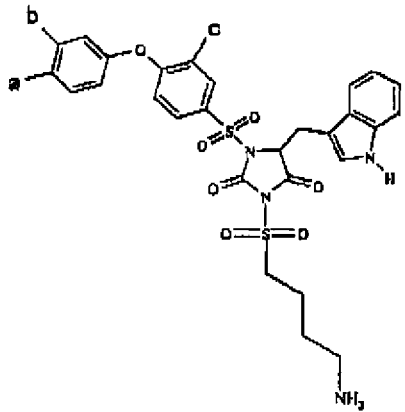    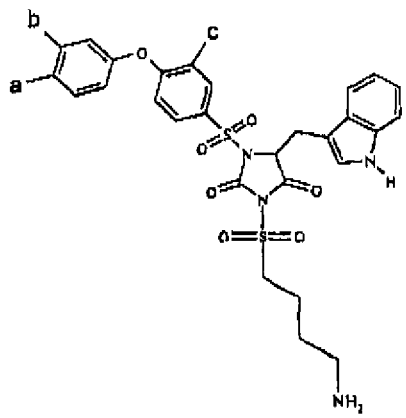

following structure wherein"                    wherein--.

Signed and Sealed this

Thirtieth Day of June, 2009

JOHN DOLL
*Acting Director of the United States Patent and Trademark Office*